(12) United States Patent
Tegg et al.

(10) Patent No.: US 8,858,495 B2
(45) Date of Patent: Oct. 14, 2014

(54) FIVE DEGREE OF FREEDOM ULTRASOUND CATHETER AND CATHETER CONTROL HANDLE

(75) Inventors: Troy T. Tegg, Elk River, MN (US);
Andrew Senn, Minneapolis, MN (US);
James V. Kauphusman, Newport Beach, CA (US); Michael C. Bednarek, Irvine, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 429 days.

(21) Appl. No.: 13/107,583

(22) Filed: May 13, 2011

(65) Prior Publication Data

US 2011/0264074 A1    Oct. 27, 2011

Related U.S. Application Data

(63) Continuation-in-part of application No. 12/346,653, filed on Dec. 30, 2008, and a continuation-in-part of application No. 11/023,667, filed on Dec. 28, 2004, now Pat. No. 7,691,095.

(60) Provisional application No. 61/334,563, filed on May 13, 2010.

(51) Int. Cl.
| | |
|---|---|
| *A61M 31/00* | (2006.01) |
| *A61B 1/005* | (2006.01) |
| *A61N 7/02* | (2006.01) |
| *A61B 5/00* | (2006.01) |
| *A61B 8/12* | (2006.01) |
| *A61B 18/18* | (2006.01) |
| *A61M 25/01* | (2006.01) |
| *A61M 37/00* | (2006.01) |
| *A61B 5/042* | (2006.01) |
| *A61B 18/14* | (2006.01) |
| *A61B 18/02* | (2006.01) |
| *A61B 19/00* | (2006.01) |
| *A61B 8/00* | (2006.01) |

(52) U.S. Cl.
CPC .......... *A61M 25/0136* (2013.01); *A61B 1/0052* (2013.01); *A61N 7/02* (2013.01); *A61B 5/6855* (2013.01); *A61B 8/12* (2013.01); *A61B 2018/0212* (2013.01); *A61B 2019/5251* (2013.01); *A61B 18/1815* (2013.01); *A61B 8/4466* (2013.01); *A61M 37/0092* (2013.01); *A61B 5/0422* (2013.01); *A61B 18/1492* (2013.01)
USPC .......... 604/95.01; 604/523; 604/528; 604/264

(58) Field of Classification Search
USPC ................ 604/523, 528, 585, 95.01, 264
See application file for complete search history.

(56) References Cited

U.S. PATENT DOCUMENTS

| | | | |
|---|---|---|---|
| 3,375,583 A | 4/1968 | Blank et al. | |
| 4,203,430 A * | 5/1980 | Takahashi ..................... | 600/149 |

(Continued)

FOREIGN PATENT DOCUMENTS

| | | |
|---|---|---|
| EP | 1205208 | 5/2002 |
| GB | 1170018 | 11/1969 |

OTHER PUBLICATIONS

"International Search Report & Written Opinion", PCT/US2012/031014 Jul. 20, 2012.

*Primary Examiner* — Scott Medway
(74) *Attorney, Agent, or Firm* — Dykema Gossett PLLC

(57) ABSTRACT

Catheter ultrasound systems including a sheath, a handle, a sheath lumen, and an ultrasound catheter disposed within the lumen of the sheath with ultrasound elements capable of visualizing anatomical regions. The handle allowing the ultrasound catheter to rotate with respect to the sheath using a rotation adjustment knob within the handle or alternatively an separate manipulation handle attached to the proximal end of the ultrasound catheter. The sheath, ultrasound catheter, or both may also include one or more electrodes or other location sensor for both orienting the ultrasound element as well as for diagnostic purposes.

15 Claims, 34 Drawing Sheets

(56) References Cited

U.S. PATENT DOCUMENTS

| | | |
|---|---|---|
| 5,167,221 A | 12/1992 | Chikama |
| 5,359,994 A | 11/1994 | Krauter et al. |
| 5,364,351 A | 11/1994 | Heinzelman et al. |
| 5,364,352 A | 11/1994 | Cimino et al. |
| 5,372,587 A | 12/1994 | Hammerslag et al. |
| 5,395,327 A | 3/1995 | Lundquist et al. |
| 5,395,328 A | 3/1995 | Ockuly et al. |
| 5,395,329 A | 3/1995 | Fleischhacker et al. |
| 5,487,757 A * | 1/1996 | Truckai et al. ................. 604/264 |
| 5,545,200 A * | 8/1996 | West et al. .................... 607/122 |
| 5,549,542 A | 8/1996 | Kovalcheck |
| 5,656,029 A | 8/1997 | Imran et al. |
| 5,662,606 A | 9/1997 | Cimino et al. |
| 5,755,760 A * | 5/1998 | Maguire et al. ............... 607/122 |
| 5,857,997 A | 1/1999 | Cimino et al. |
| 5,861,024 A | 1/1999 | Rashidi |
| 5,938,616 A | 8/1999 | Eaton et al. |
| 5,957,943 A | 9/1999 | Vaitekunas |
| 6,024,722 A | 2/2000 | Rau et al. |
| 6,171,277 B1 | 1/2001 | Ponzi |
| 6,183,435 B1 | 2/2001 | Bumbalough |
| 6,198,974 B1 | 3/2001 | Webster, Jr. |
| 6,200,315 B1 | 3/2001 | Gaiser |
| 6,203,507 B1 | 3/2001 | Wadsworth |
| 6,203,525 B1 | 3/2001 | Whayne |
| 6,210,362 B1 | 4/2001 | Ponzi |
| 6,210,407 B1 | 4/2001 | Webster |
| 6,214,002 B1 | 4/2001 | Fleischman |
| 6,221,087 B1 | 4/2001 | Anderson |
| 6,224,587 B1 | 5/2001 | Gibson |
| 6,241,754 B1 | 6/2001 | Swanson |
| 6,308,091 B1 | 10/2001 | Avitall |
| 6,375,654 B1 | 4/2002 | McIntyre |
| 6,430,426 B2 | 8/2002 | Avitall |
| 6,454,758 B1 | 9/2002 | Thompson |
| 6,468,260 B1 | 10/2002 | Bumbalough et al. |
| 6,485,455 B1 | 11/2002 | Thompson et al. |
| 6,500,167 B1 | 12/2002 | Webster |
| 6,544,215 B1 | 4/2003 | Bencini et al. |
| 6,554,794 B1 | 4/2003 | Mueller et al. |
| 6,582,536 B2 | 6/2003 | Shimada |
| 6,602,242 B1 | 8/2003 | Fung et al. |
| 6,652,506 B2 | 11/2003 | Bowe et al. |
| 6,829,497 B2 | 12/2004 | Mogul |
| 6,913,594 B2 | 7/2005 | Coleman et al. |
| 6,991,616 B2 | 1/2006 | Bencini et al. |
| 7,056,314 B1 * | 6/2006 | Florio et al. ................. 604/528 |
| 7,263,397 B2 | 8/2007 | Hauck |
| 7,269,453 B2 | 9/2007 | Mogul |
| 7,374,553 B2 | 5/2008 | Koerner et al. |
| 7,386,339 B2 | 6/2008 | Strommer |
| 7,416,547 B2 | 8/2008 | Hill et al. |
| 7,615,044 B2 * | 11/2009 | Scheibe et al. ................ 604/528 |
| 7,691,095 B2 | 4/2010 | Bednarek |
| 7,803,130 B2 * | 9/2010 | Ryan et al. ................. 604/95.04 |
| 2007/0299424 A1 | 12/2007 | Cumming |
| 2008/0009745 A1 | 1/2008 | Hossack et al. |
| 2008/0119727 A1 | 5/2008 | Barbagli et al. |
| 2009/0105640 A1 | 4/2009 | Bednarek |
| 2010/0069921 A1 | 3/2010 | Miller |
| 2010/0168735 A1 | 7/2010 | Deno |
| 2010/0217235 A1 | 8/2010 | Thorstenson et al. |

* cited by examiner

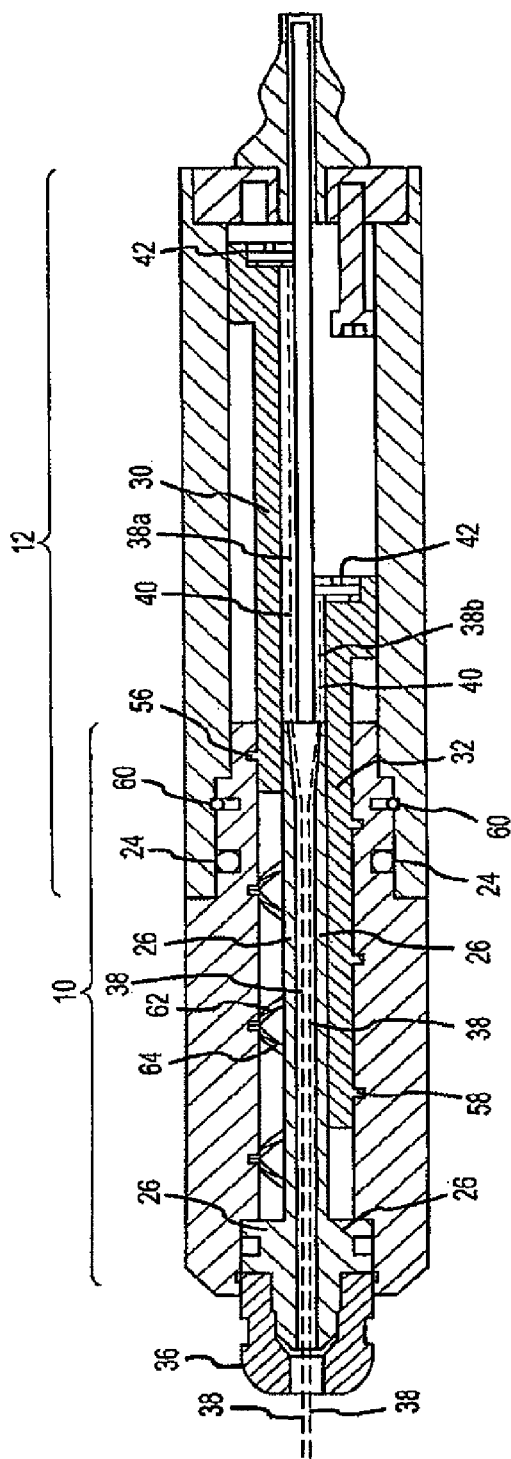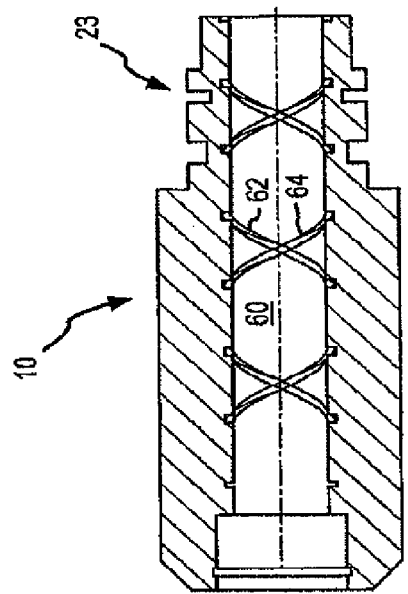
FIG.10
FIG.11

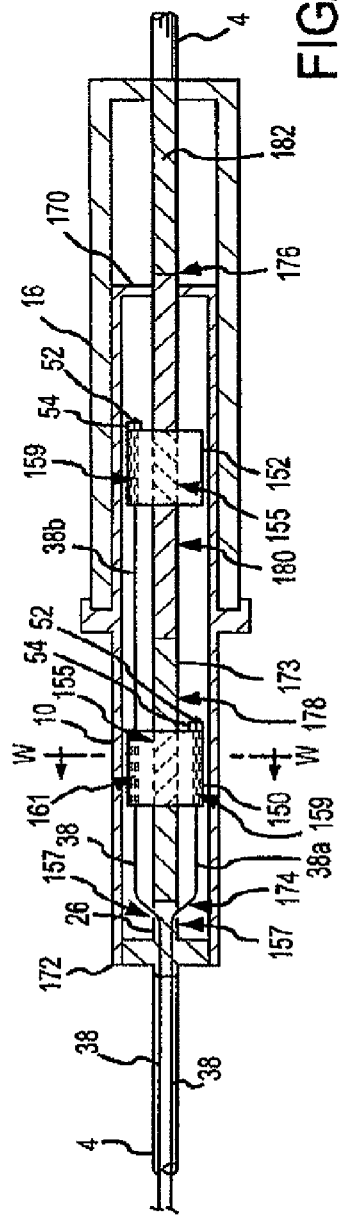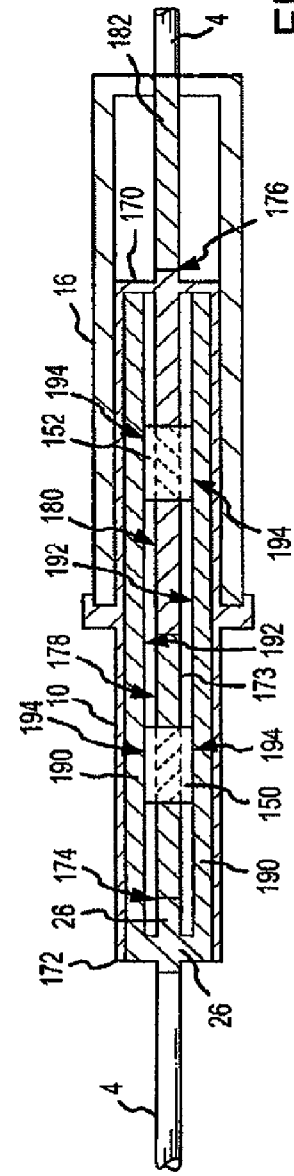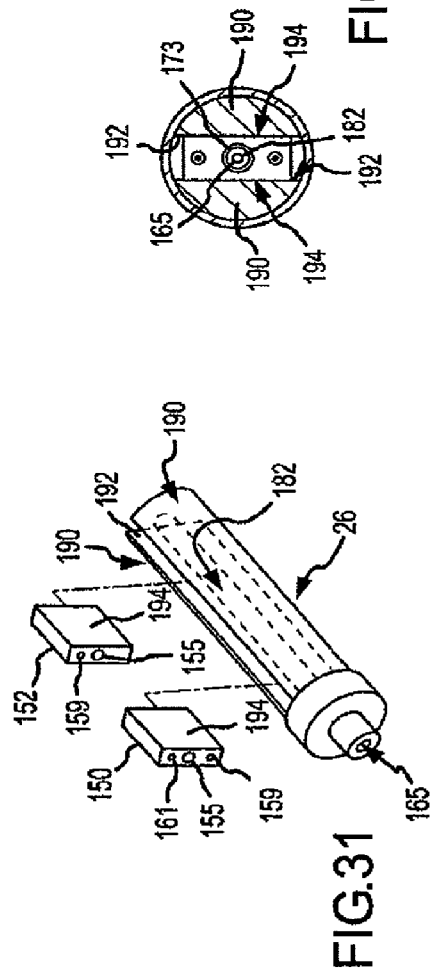

FIVE DEGREE OF FREEDOM ULTRASOUND CATHETER AND CATHETER CONTROL HANDLE

CROSS-REFERENCE TO RELATED APPLICATIONS

This application claims the benefit of U.S. Application No. 61/334,563 ("the '563 application") filed May 13, 2010. This application is a Continuation In Part of U.S. Non-provisional Application No. 12/346,653 ("the '653 application"), filed Dec. 30, 2008, which is a Continuation of U.S. Non-Provisional Application No. 11/023,667 ("the '667 application"), filed Dec. 28, 2004, now U.S. Pat. No. 7,691,095. This application claims the benefit of each of the '563 application, the '653 application, and the '667 application, each of which are hereby incorporated by reference as if fully set forth herein.

BACKGROUND OF THE INVENTION a. Field of the Invention

The present invention relates to ultrasound catheters and sheaths and methods of using ultrasound catheters and sheaths. More particularly, the present invention relates to a control handle for steerable sheaths, methods of manufacturing and using such a handle, an ultrasound catheter for use with the steerable sheath, and methods of using the combination of the ultrasound catheter and sheath.

b. Background Art

Catheters (i.e. catheters or sheaths) that have flexible tubular bodies with deflectable distal ends and control handles for controlling distal end deflection are used for many invasive medical procedures. For example, catheters having conductive electrodes along the distal ends of their bodies are commonly used for intra-cardiac electrophysiology studies. The distal end of a catheter body is typically placed into a patient's heart to monitor and/or record the intra-cardiac electrical signals during electrophysiology studies or during intra-cardiac mapping. The orientation or configuration of the distal end is controlled via an actuator located on the catheter's control handle, which remains outside the patient's body. The electrodes conduct cardiac electrical signals to appropriate monitoring and recording devices that are operatively connected at the control handle.

Typically, a catheter body is cylindrical and electrically non-conductive. The catheter body includes a flexible tube constructed from polyurethane, nylon or other electrically non-conductive flexible material. The catheter body further includes braided steel wires or other non-metallic fibers in its wall as reinforcing elements. Each electrode has a relatively fine electrically conductive wire attached thereto and extending through the catheter body. The conductive wire extends from the distal end to a proximal end where electrical connectors such as plugs or jacks are provided to be plugged into a corresponding socket provided in a recording or monitoring device.

The distal portion of the catheter body is selectively deformed into a variety of curved configurations using the actuator on the control handle. The actuator is commonly internally linked to the distal portion of the catheter body by at least one deflection wire. Some catheter bodies employ a single deflection wire, which is pulled (i.e. placed in tension) by the actuator in order to cause the distal portion of the catheter body to deform. Other catheter bodies have at least two deflection wires, where the displacement of one wire (i.e., placing one wire in tension) results in the other wire going slack (i.e., the wire does not carry a compressive load). In such catheters, where the deflection wires are not adapted to carry compressive loads (i.e., the deflection wires are only meant to be placed in tension), the deflection wires are commonly called pull or tension wires.

Prior art control handles are often inadequate with respect to their ability to provide the finely controlled deflection adjustment for the distal end of the catheter body necessary to target a particular anatomy with an ultrasound catheter. The prior art control handles often provide inadequate deflection wire travel for a desired viewing angle or orientation. The control handles often have a mechanical advantage that is less than desirable and, as a result, require significant effort to operate on the part of a user. Moreover, it is desirable that the physician be able to set the ultrasound catheter at a particular viewing angle and have it stay set. However, with prior art catheters the control handles typically require the physician to take a conscious step to maintain the catheter at the desired deflection.

One type of instrument catheter is an ultrasound visualization catheter, such as an intracardiac echocardiography (ICE) catheter, which includes ultrasound elements or arrays on the distal end of the catheter. The ultrasound elements are useful for visualizing particular portions of the cardiac anatomy under study. The typical ultrasound catheter aims a two dimensional beam or fan at a portion of the anatomy and provides the clinician with a visual of the anatomy under study. Because the fan may be both narrow and small, and of limited range, precise adjustments are often necessary in order to successfully view particular anatomy. Thus, the ability to adjust the orientation or direction of an ultrasound fan precisely, with minimal or no deformation of the catheter, is important in using an ultrasound catheter. Providing a handle with fine motor control and a desirable mechanical advantage also has specific utility for an ultrasound catheter. In particular, there is a need in the art for a catheter system that offers improved operation and deflection adjustment of the distal end of the ultrasound catheter body. There is also a need in the art for a method of manufacturing and using such a catheter system.

BRIEF SUMMARY OF THE INVENTION

A catheter system may include a fixed dimensional and bi-directional steerable catheter control handle having an apparatus for imparting a tensile force to deflect a distal portion of a catheter while maintaining its exterior dimensions. The apparatus may include a handle grip including generally oval or circular cross-sections of generally predetermined exterior dimensions, and a longitudinal axis. A flexible member may include proximal and distal end portions, with the proximal end portion being coupled to the handle grip. An actuator may include a generally circular cross-section of generally predetermined exterior dimensions, and may be rotatably coupled to the handle grip around the longitudinal axis of the handle grip. One or more deflection wires may be operably coupled to the actuator and to the distal end portion of the flexible member such that rotation of the actuator imparts a tensile force to the deflection wires thereby causing the distal end portion of the flexible member to deflect from a prior configuration while maintaining the generally predetermined exterior dimensions of the handle grip and the actuator.

For the system described above, in an embodiment, the system may include means for simultaneously imparting a tensile force to the first deflection wire and releasing a tensile force on the additional deflection wire. The actuator may include an interior surface forming an aperture generally orthogonally oriented with respect to the longitudinal axis of the handle grip, with the interior surface including one or more sets of threaded grooves which cooperate with the means. The means may include a pair of generally axially displaceable members disposed within the handle grip, and rotation of the actuator may impart opposing forces to the axially displaceable members.

For the apparatus described above, in an embodiment, the flexible body may include one or more longitudinal lumens. In an embodiment, the apparatus may include one or more electrodes coupled to the flexible body. The flexible body, in an embodiment, may include a biocompatible electrically insulative material. The electrically insulative material may be a flexible material. Alternatively, the electrically insulative material may include a polyurethane material or a nylon material. The apparatus, in an embodiment, may include one or more reinforcing elements disposed within a portion of the flexible member. The reinforcing element may include braided members, which may include a conductive material.

For the apparatus described above, in an embodiment, the flexible body may include a segment of a braided metallic wire and/or a non-metallic fiber. The apparatus, in an embodiment, may include a hemostasis valve coupled to the handle grip. In an embodiment, an exterior surface of the actuator may include a generally longitudinal groove and/or a generally longitudinal protuberance.

In one embodiment, the invention comprises an ultrasound catheter system including a sheath or guiding catheter having a flexible body with a lumen running completely through it. The flexible body having a distal end connected to one or more deflection wires and a proximal end portion coupled to a handle. The handle comprising a actuator, a second actuator and a handle grip with a lumen running completely through the handle that, combined with the lumen of the guiding catheter, creates a continuous lumen from the guiding catheter's distal end to the proximal end of the handle. In some embodiments the actuators are adjustment knobs capable of pivoting about the longitudinal axis of the handle. The handle also contains a plurality of slides attached to the deflection wires of the guiding catheter. The slides being disposed such that rotation of the first actuator causes the deflection members to displace axially within the handle grip placing at least one deflection wire in tension thereby deflecting the distal end of the guiding catheter. The handle also contains a rotation assembly operably connected to the second actuator.

An instrument catheter having an elongate body with a instrument element attached to its distal end, such as an ICE catheter, can be disposed within the continuous lumen such that the instrument element extends beyond the distal end of the guiding catheter and the proximal portion of the elongate body is attached to the rotation assembly. In one embodiment, the instrument element can be an ultrasound element, such as a linear phased array. In another embodiment, the instrument element can be a therapeutic instrument, such as an ablation element. The instrument catheter can be a diagnostic catheter, such as an ultrasound catheter, or a therapeutic catheter, such as an ablation catheter.

Rotation of the second actuator about the longitudinal axis causes the rotation assembly to rotate the instrument catheter about the longitudinal axis. In an embodiment, the rotation assembly rotates the instrument catheter through the same angular displacement as the second actuator is rotated. In another embodiment, the rotation assembly rotates the instrument catheter in the same direction about the longitudinal axis as the second actuator is rotated. In yet another embodiment, the rotation assembly includes a drive gear operably connected to the second actuator, one or more ratio gears that transmit torque received by the drive gear from the second actuator to a positioning gear. The positioning gear being coupled to the proximal end portion of the instrument catheter, thereby causing the instrument catheter to rotate with the positioning gear. In another embodiment, the rotation assembly may contain a tube attached to the positioning gear that passes through the rotation assembly as part of the continuous lumen. In such an embodiment, a instrument catheter may be attached to the inner surface of the tube to cause it to rotate with the tube in response to the rotation of the second actuator.

In one embodiment, the distal end portion of the instrument catheter contains one or more location sensors, such as electrodes or magnetic coils to aid in the location and orientation of the distal end portion. In another embodiment, the location sensors may be operably connected to an electroanatomical mapping system.

In another embodiment, the handle can include an irrigation lumen coupled to the proximal end of the guiding catheter that maintains a fluid relationship with the lumen of the guiding catheter.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 10 is a longitudinal sectional plan view of the handle taken along section line BB or FIG. 9.

FIG. 11 is a longitudinal sectional plan view of the knob taken along section line BB in FIG. 9.

FIG. 29 is a longitudinal sectional elevation of another embodiment of the handle taken along section line YY of FIG. 23.

FIG. 30 is a longitudinal sectional plan view of the handle depicted in FIG. 29 taken along section line W in FIG. 23 and wherein section line VV forms a plane that is perpendicular to the plane formed by section line YY in FIG. 23.

FIG. 31 is an isometric view of one embodiment of the wire guide.

FIG. 32 is a latitudinal sectional elevation of the handle as taken along section line WW in FIG. 29.

DETAILED DESCRIPTION OF THE INVENTION

Figure 1:
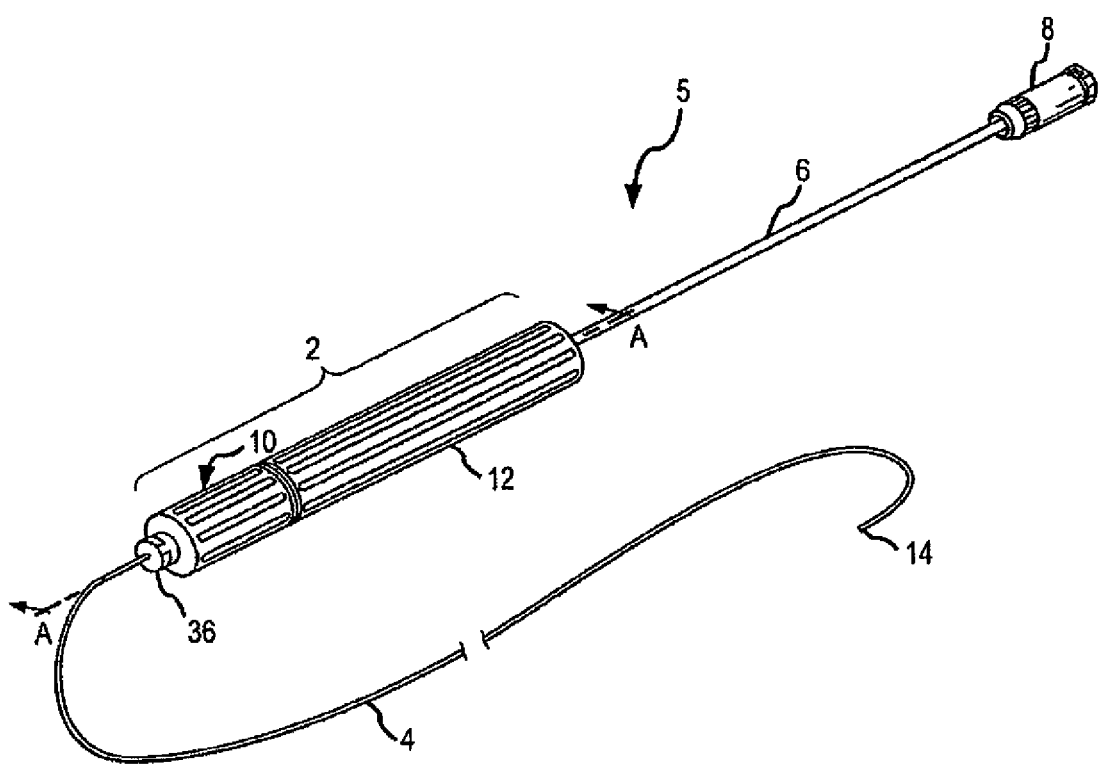
FIG. 1 is an isometric view of one embodiment of the present invention, which is a control handle for a catheter or sheath.

Referring to FIG. 1, one embodiment of the present invention having a control handle 2 for a flexible tubular body 4 of a catheter 5 is depicted in an isometric view. Throughout this specification, the term catheter is meant to include, without limitation, catheters, sheaths and similar medical devices. As shown in FIG. 1, in one embodiment of the present invention, the distal end of the handle 2 is connected to the catheter body 4 and the proximal end of the handle 2 is connected to tubing 6 that contains electrical wire and extends to an electrical connector 8. The handle 2 includes an actuator 10 depicted as an adjustment knob and a handle grip 12. For clarity, the actuator 10 will be referred to as an adjustment knob, but the actuator 10 may also be a dial, lever, switch, or other device for receiving input from a user without departing from the spirit and scope of the invention. As will become clear from this specification, the handle 2 of the present invention is advantageous in that it is compact and allows a user to manipulate the catheter body's extreme distal end 14 is a bi-directional manner by pivoting the adjusting knob 10 relative to the handle grip 12 in one direction or the other about the longitudinal axis of the handle 2. Furthermore, in one embodiment, the handle 2 has a lumen that runs uninterrupted from the proximal end of the handle 2 to the extreme distal end 14 of the catheter body 4. This lumen can be used to provide contrast injection for guide wire insertion.

Figure 2:
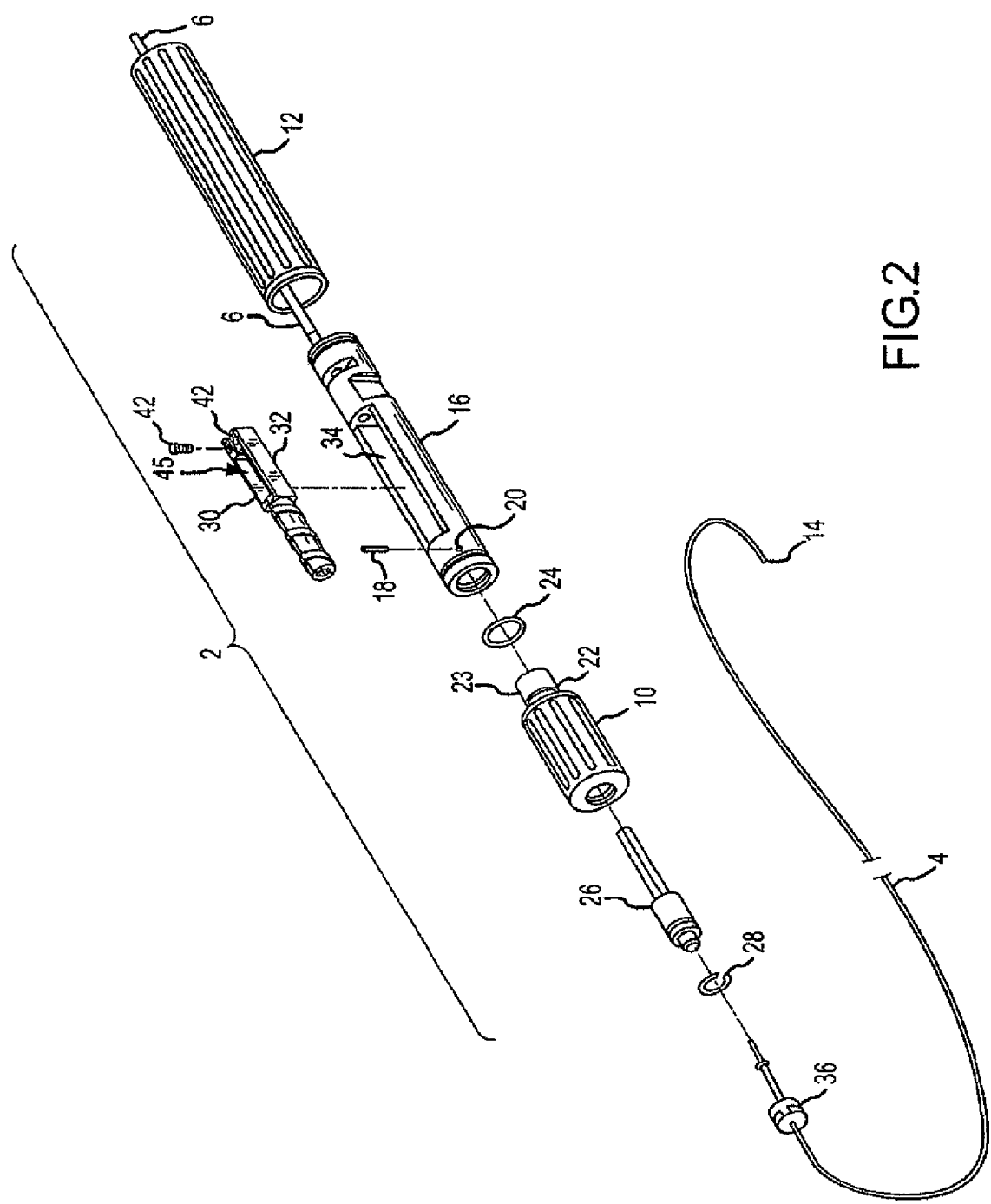
FIG. 2 is an isometric view of the handle exploded to show its various components.
Figure 3:
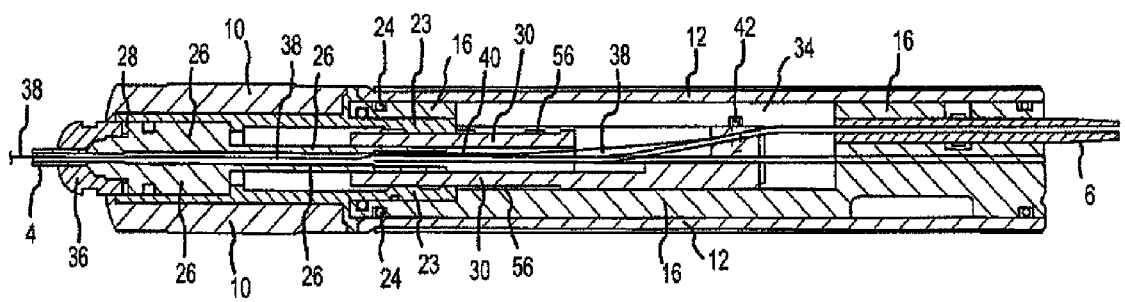
FIG. 3 is a longitudinal sectional elevation of the handle taken along section line AA of FIG. 1.

For a more detailed discussion of the handle 2, reference is now made to FIGS. 2 and 3. FIG. 2 is an isometric view of handle 2 exploded to show its various components. FIG. 3 is a longitudinal sectional elevation of the handle 2 taken along section line AA of FIG. 1.

As shown in FIGS. 2 and 3, the adjusting knob 10 is pivotally attached to a mounting shaft (i.e., a slide base or base portion) 16 contained within the handle grip 12. To pivotally attach the knob 10 to the mounting shaft 16, a dowel pin 18 is inserted into a pinhole 20 in the distal end of the shaft 16 and mates with a groove 22 in a hub portion 23 of the knob 10. A silicone o-ring 24 exists between the hub portion 23 of the knob 10 and the distal end of the shaft 16.

As indicated in FIGS. 2 and 3, a wire guide 26 is positioned within the adjusting knob 10 and is held in place by a retaining ring 28. A right slide or member 30 and a left slide or member 32 are slideably positioned within a slot (i.e., a slide compartment) 34 in the mounting shaft 16. A catheter body-retaining nut 36 is used to secure the catheter body 4 to the distal end of the wire guide 26.

As illustrated in FIG. 3, a pair of deflection wires 38 extend from the extreme distal end 14 of the body 4, through the body 4, the wire guide 26 and a passage 40 formed between the two slides 30, 32, to a point near a proximal portion of the slides 30, 32. Each wire 38 then affixes to an individual slide 30, 32 via a retention screw 42.

Figure 4:
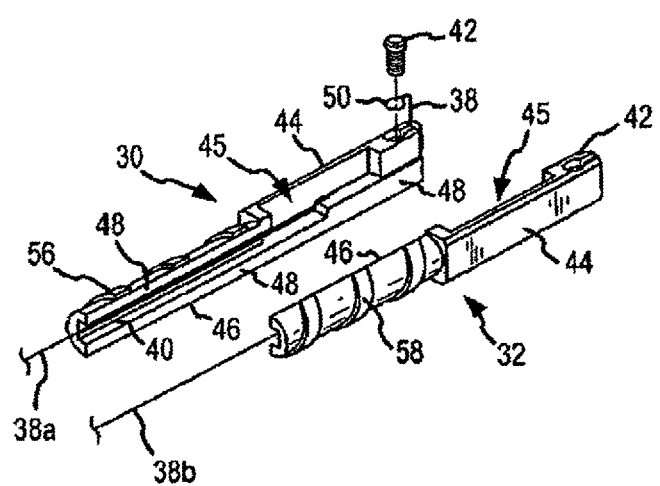
FIG. 4 is an isometric view of the right and left slides with their respective deflection wires attached.

For a more detailed discussion of the slides 30, 32 and their relationship to the deflection wires 38, reference is now made to FIG. 4, which is an isometric view of the deflection wires 38a, 38b attached to the right and left slides 30, 32. As shown in FIG. 4, the slides 30, 32, which are mirror images of each other, each have a rectangular box-like proximal portion 44 and a half-cylinder distal portion 46. Each proximal portion 44 has a generally planar sides and bottom of the slot 34, which act as thrust surfaces for the slides 30, 32.

Each half-cylinder distal portion 46 is hollowed out along its longitudinal axis to form the passage 40 through which the deflection wires 38a, 38b and, as indicated in FIG. 3, the narrow proximal portion of the wire guide 26 extend when the slides 30, 32 are in the assembled handle 2. Each slide 30, 32 has a planar slide face 48 that is meant to slideably abut against the planar slide face 48 of the opposing slide 30, 32. Thus, as illustrated in FIG. 2, when the planar slide faces 48 of the slides 30, 32 abut against each other and the extreme proximal ends of each slide 30, 32 are flush with each other, the half-cylinder distal portions 46 of each slide 30, 32 combine to form a complete cylinder with a channel or passage 40 there through.

Figure 5:
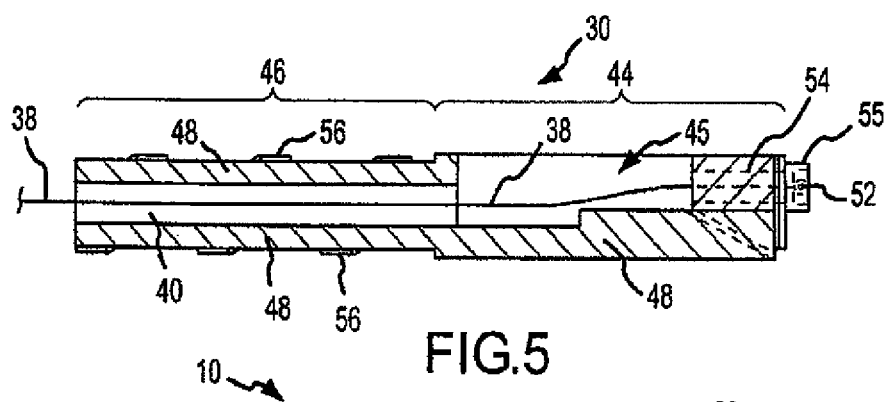
FIG. 5 is a side elevation of an exemplary slide illustrating a means of securing a deflection wire to the proximal end of the slide.

As shown in FIG. 4, in one embodiment, the proximal ends of each deflection wire 38a, 38b forms a loop 50 through which a retention screw 42 passes to secure the wire 38a, 38b to the proximal portion of the respective slide 30, 32. As indicated in FIG. 5, which is a side elevation of an exemplary slide 30, in one embodiment, the proximal end of each deflection wire 38 forms a knot 52. The wire 38 passes through a hollow tension adjustment screw 54 and the knot 52 abuts against the head 55 of screw 54, thereby preventing the wire 38 from being pulled back through the screw 54. In one embodiment, the screw's longitudinal axis and the longitudinal axis of the slide 30, 32 are generally parallel. Each tension adjustment screw 54 is threadably received in the proximal end of its respective slide 30, 32. Tension in a wire 38 may be increased by outwardly threading the wire's tension adjustment screw 54. Conversely, tension in a wire 38 may be decreased by inwardly threading the wire's tension adjustment screw 54.

As can be understood from FIG. 4, in one embodiment where the wires 38a, and 38b are intended to only transmit tension forces, the wires 38a, 38b may deflect or flex within an open area 45 defined in the proximal portion 44 of each slide 30, 32 when the slides 30, 32 displace distally. Similarly, as can be understood from FIG. 5, in another embodiment where the wires 38 are intended only to transmit tension forces, the wires 38 may slide proximally relative to the screw 54 when the slides 30, 32 displace distally.

As shown in FIG. 4, in one embodiment, the outer circumference of the half-cylinder distal portion 46 of the right slide 30 is threaded with a right-hand thread 56, and the outer circumference of the half-cylinder distal portion 46 of the left slide 32 is threaded with a left-hand thread 58. In one embodiment, the outer circumference of the half-cylinder distal portion 46 of the right slide 30 is threaded with a left-hand thread, and the outer circumference of the half-cylinder distal portion 46 of the left slide 32 is threaded with a right-hand thread.

Figure 6:
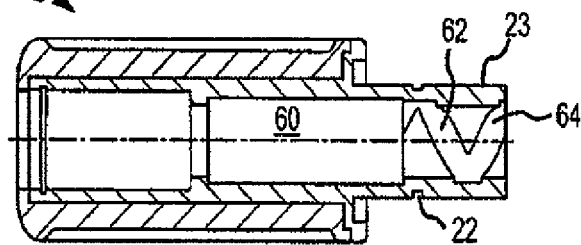
FIG. 6 is a longitudinal sectional elevation of the adjusting knob taken along section line AA of FIG. 1.

For a better understanding of the relationship of the slide threads 56, 58 to the rest of the handle 2, reference is now made to FIG. 6, which is a longitudinal sectional elevation of the adjusting knob 10 taken along section line AA of FIG. 1. As indicated in FIG. 6, a cylindrical hole or shaft 60 passes through the knob 10 along the knob's longitudinal axis. In the hub portion 23 of the knob 10, the inner circumferential surface of the shaft 60 has both right hand threads 62 and left hand threads 64. These internal threads 62, 64 of the knob 10 mate with the corresponding external threads 56, 58 of the slides 30, 32. More specifically, the right internal threads 62 of the knob 10 mate with the right external threads 56 of the right slide 30, and the left internal threads 64 of the knob 10 mate with the left external threads 58 of the left slide 32.

Thus, as can be understood from FIGS. 2, 3, 4, and 6, in one embodiment, as the knob 10 is rotated clockwise relative to the longitudinal axis of the handle 2, the internal and external right threads 62, 56 engage and the internal and external left threads 64, 58 engage, thereby causing simultaneous opposed displacement of the right and left slides 30, 32 longitudinally within the slot 34 in the handle 10. Specifically, because of the threading arrangement of the knob 10 and the slides, 30, 32, the right slide 30 moves distally within the slot 34 and the left slide 32 moves proximally within the slot 34 when the knob 10 is rotated clockwise relative to the handle grip 12 of the handle 2. Conversely, when the knob 10 is rotated in a counterclockwise manner relative to the handle grip 12 of the handle 2, the right slide 30 moves proximally within the slot 34 and the left slide 32 moves distally within the slot 34.

As can be understood from FIGS. 4 and 6, when the knob 10 is rotated such that the right slide 30 is urged distally and the left slide 32 is urged proximally, the deflection wire 38a connected to the right slide 30 is placed into compression and the deflection wire 38b connected to the left slide 32 is placed into tension. This causes the extreme distal end 14 of the catheter body 4 to deflect in a first direction. Conversely, when the knob 10 is rotated such that the right slide 30 is urged proximally and the left slide 32 is urged distally, the deflection wire 38a connected to the right slide 30 is placed into tension and the deflection wire 38b connected to the left slide 32 is placed into compression. This causes the extreme distal end 14 of the catheter body 4 to deflect in a second direction that is opposite the first direction.

The control handle 2 of the present invention as described has several advantages. First, the handle 2 is compact and may be operated with a single hand, allowing the clinician to keep a second hand free or on a second device. Second, the threaded slides 30, 32 and knob 10 allow a physician to make fine, controlled adjustments to the bend in the distal end 14 of the catheter body 4. Third, once the knob 1- is rotated so as to cause a bend in the distal end 14 of the catheter body 4, the threads 56, 58, 62, 64 interact to maintain the bend without requiring any action on the physician's part. Fourth, because the slides 30, 32 simply displace distally and proximally along the longitudinal axis of the handle 2, they are less likely to permanently deform the wires 38 as compared to the wire displacement mechanisms in some prior art handles. Fifth, the threads 56, 58, 62, 64 are mechanically advantageous in that they provide increased deflection wire travel and reduced actuation effort for the physician, as compared to some prior art handles.

Figure 33:
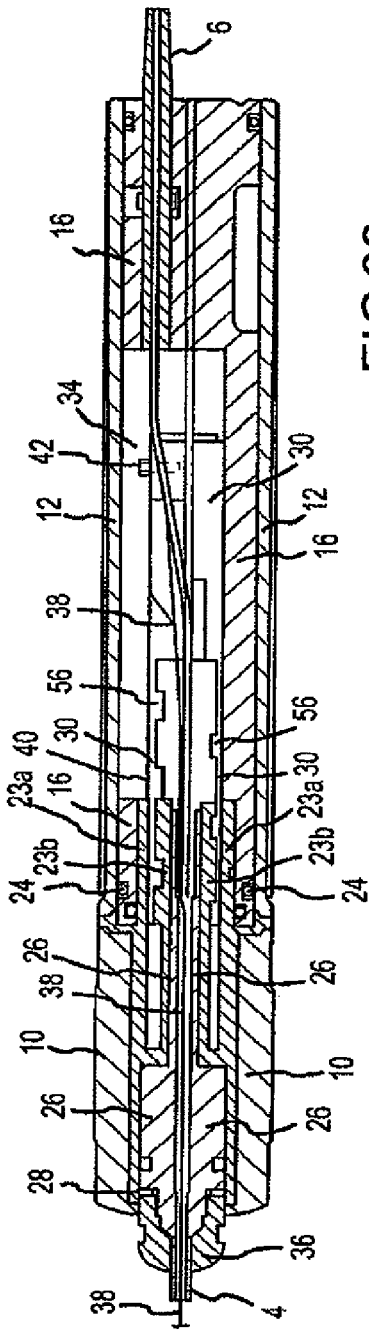
FIG. 33 is a longitudinal sectional elevation of the handle taken along section line AA of FIG. 1.
Figure 34:
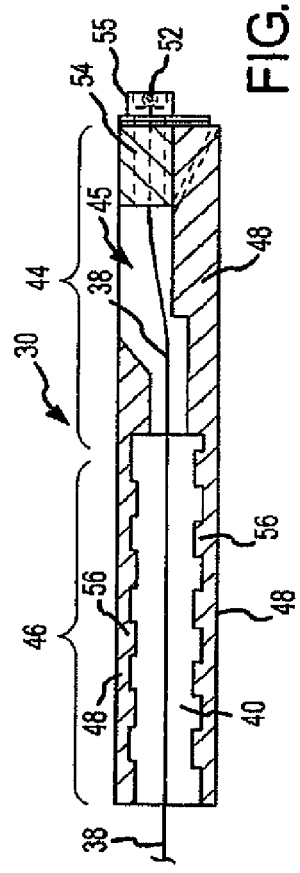
FIG. 34 is a side elevation of an exemplary slide employed in the embodiment depicted in FIG. 33.
Figure 35:
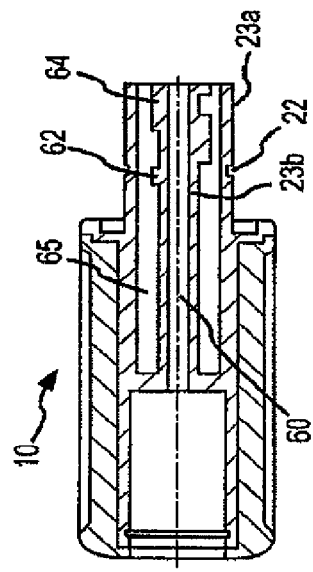
FIG. 35 is a longitudinal section elevation of the adjusting knob taken along section line AA of FIG. 1.

While FIGS. 2-6 depict an embodiment where the slides 30, 32 have external threads 56, 58 and the knob 10 has internal threads 62, 64, in other embodiments the threading arrangement is reversed. For a discussion of one such embodiment, reference is made to FIGS. 33-35. FIG. 33 is a longitudinal sectional elevation of the handle 2 taken along section line AA of FIG. 1. FIG. 34 is a side elevation of an exemplary slide employed in the embodiment depicted in FIG. 33. FIG. 35 is a longitudinal sectional elevation of the adjusting knob taken along section line AA of FIG. 1.

A comparison of the embodiment depicted in FIGS. 33-35 to the embodiment depicted in FIGS. 3, 5, and 6 reveals that the two embodiments are generally the same, except as will be described in the following discussion of FIGS. 33-35. Reference numbers utilized in FIGS. 33-35 pertain to the same or similar features identified by the same reference numbers in FIGS. 3, 5, and 6.

As shown in FIG. 33, the adjusting knob 10 is pivotally attached to a mounting shaft (i.e., a slide base or base portion) 16 contained within the handle grip 12. A wire guide 26 is positioned within the adjusting knob 10. like the embodiment depicted in FIG. 2, the embodiment illustrated in FIG. 33 includes a right slide or member 30 and a left slide or member 32 that are slideably positioned within a slot (i.e., a slide compartment) 34 in the mounting shaft 16.

As can be understood from FIG. 34, the slides 30, 32, which are mirror images of each other, each have a rectangular box-like proximal portion 44 and a distal portion 46 that may be rectangular or half-cylindrical. Each proximal portion 44 has a generally planar outer sidewall and bottom wall. These planar surfaces slideably displace against the generally planar sides and bottom of the slot 34, which act as thrust surfaces for the slides 30, 32.

Each distal portion 46 is hollowed out to form half of a cylindrical passage 40 that is created when the slides 30, 32 are abutted against each other in a side-by-side relationship. Thus, each distal portion 46 of each slide 30, 32 includes an inner circumferential surface, which when combined with the inner circumferential surface of the other slide 30, 32, defines the cylindrical passage 40.

As indicated in FIG. 34, in one embodiment, the inner circumferential surface of the right slide 30 is threaded with a right-hand thread 56. Similarly, as can be understood from FIG. 34, the inner circumferential surface of the left slide 32 is threaded with a left-hand thread 58. Thus, the distal portion 46 of each slide 30, 32 is equipped with internal threads. In another embodiment, the inner circumferential surface of the right slide 30 is threaded with a left-hand thread 58. Similarly, the inner circumferential surface of the left slide 32 is threaded with a right-hand thread 56.

As indicated in 35, the knob 10 includes an outer hub 23a surrounding an inner hub 23b. A space 65 exists between, and is defined by, the inner and outer hubs 23a, 23b. The space 65 is adapted to receive the distal ends 46 of each slide 30, 32. The outer circumferential surface of the inner hub 23b has both right hand threads 62 and left hand threads 64. These external threads 62, 64 of the knob 10 mate with the corresponding internal threads 56, 58 of the slides 30, 32. More specifically, the right external threads 62 of the knob 10 mate with the right internal threads 56 of the right slide 30, and the left external threads 64 of the knob 10 mate with the left internal threads 58 of the left slide 32.

As can be understood from FIG. 33, in one embodiment, as the knob 10 is rotated clockwise relative to the longitudinal axis of the handle 2, the internal and external right threads 56, 62 engage and the internal and external left threads 58, 64 engage, thereby causing simultaneous opposed displacement of the right and left slides 30, 32 longitudinally within the slot 34 in the handle 10. Specifically, because of the threading arrangement of the knob 10 and the slides, 30, 32, the right slide 30 moves distally within the slot 34 and the left slide 32 moves proximally within the slot 34 when the knob 10 is rotated clockwise relative to the handle grip 12 of the handle 2. Conversely, when the knob 10 is rotated in a counterclockwise manner relative to the handle grip 12 of the handle 2, the right slide 30 moves proximally within the slot 34 and the left slide 32 moves distally within the slot 34.

As can be understood from FIG. 33, when the knob 10 is rotated such that the right slide 30 is urged distally and the left slide 32 is urged proximally, the deflection wire 38 connected to the right slide 30 is placed into compression and the deflection wire 38 connected to the left slide 32 is placed into tension. This causes the extreme distal end 14 of the catheter body 4 to deflect in a first direction. Conversely, when the knob 10 is rotated such that the right slide 30 is urged proximally and the left slide 32 is urged distally, the deflection wire 38 connected to the right slide 30 is placed into tension and the deflection wire 38 connected to the left slide 32 is placed into compression. This causes the extreme distal end 14 of the catheter body 4 to deflect in a second direction that is opposite the first direction.

Figure 7:
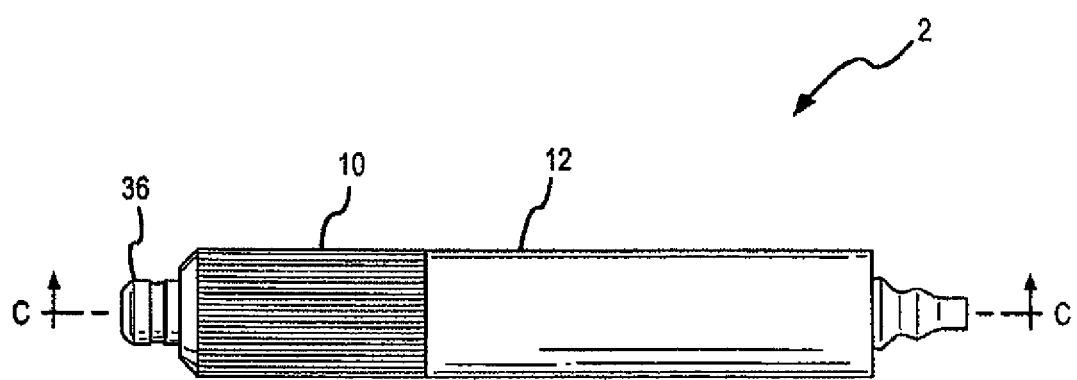
FIG. 7 is a plan view of another embodiment of the handle.
Figure 8:
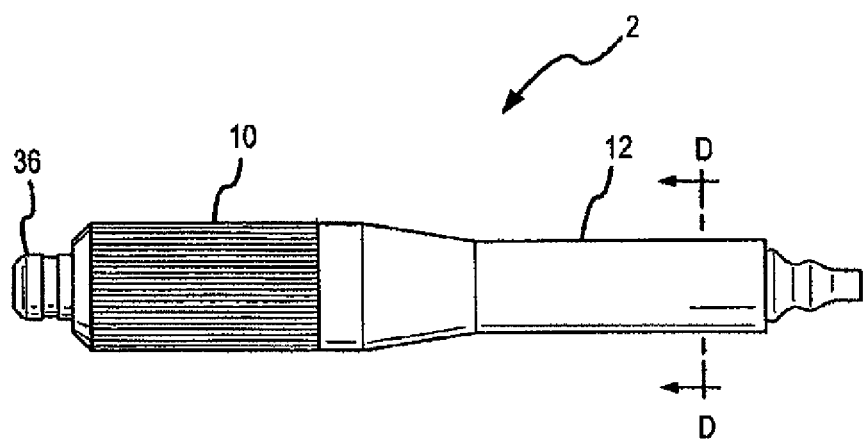
FIG. 8 is a side elevation of the handle depicted in FIG. 7.
Figure 9:
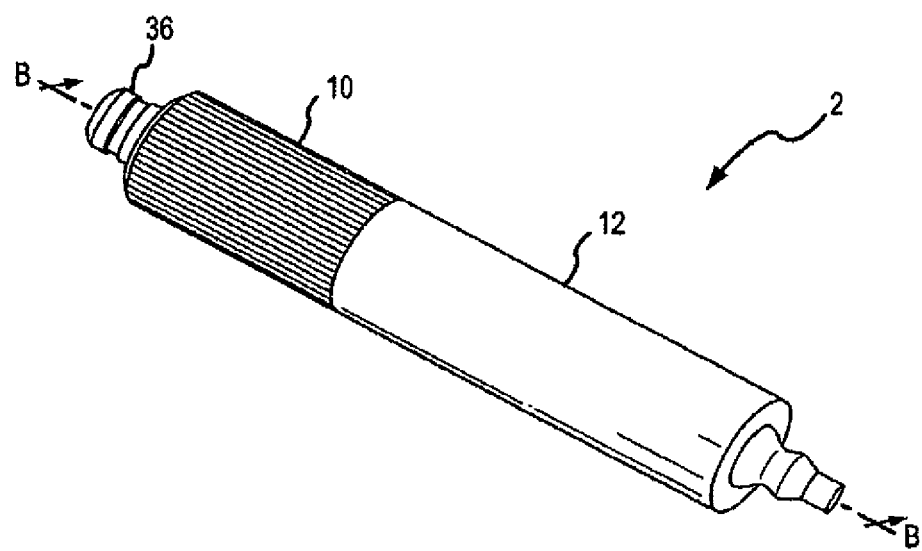
FIG. 9 is an isometric view of the distal end of the handle depicted in FIG. 7.

For a detailed discussion of another embodiment of the handle 2 of the present invention, reference is now made to FIGS. 7, 8, and 9. FIG. 7 is a plan view of the handle 2. FIG. 8 is a side elevation of the handle 2. FIG. 9 is an isometric view of the distal end of the handle 2.

As shown in FIGS. 7-9, the handle 2 includes an adjusting knob 10 on its distal end and a handle grip 12 on its proximal end. As can be understood from FIGS. 7-9, in one embodiment, the knob 10 has a generally circular cross-section and the handle grip 12 has a generally oval cross-section. In one embodiment, both the knob 10 and the handle grip 12 have generally circular cross-sections. The oval cross-section of the handle grip 12 is advantageous because it provides the physician with a tactile indication of the catheter's rotational position.

For a more detailed discussion f the components of the handle 2, reference is now made to FIG. 10, which is a longitudinal sectional plan view of the handle 2 taken along section line BB of FIG. 9. As shown in FIG. 10, an o-ring 24 is located between the handle grip 12 and a groove in the knob 10. The knob 10 is pivotally affixed to the handle grip 12 via a rotating retaining-ring 60 that resides within grooves in both the knob and the handle grip 12.

As illustrated in FIG. 10, a catheter body-retaining nut 36 is threadably affixed to the distal end of a wire guide 26 that extends along the axial center of the knob 10. As indicated in FIG. 10 and more clearly shown in FIG. 11, which is a longitudinal sectional plan view of the knob 10 taken along section line BB in FIG. 9, a cylindrical hole or shaft 60 passes through the knob 10 along the knob's longitudinal axis. The inner circumferential surface of the shaft 60 has both right hand threads 62 and left hand threads 64 that extend towards the distal end of the knob 10 from a hub portion 23 of the knob 10. As shown in FIG. 11, in one embodiment, the knob 10 is a singular integral piece.

Figure 12:
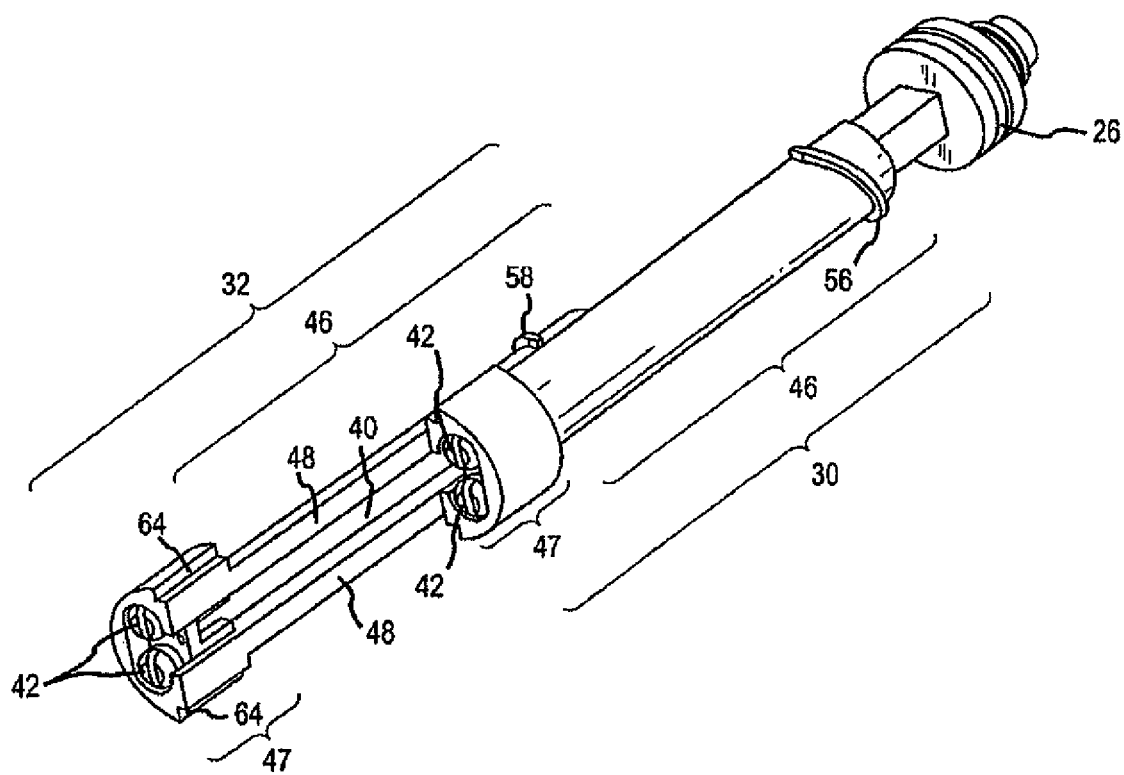
FIG. 12 is a right side view of the slides displaced about the wire guide.
Figure 13:
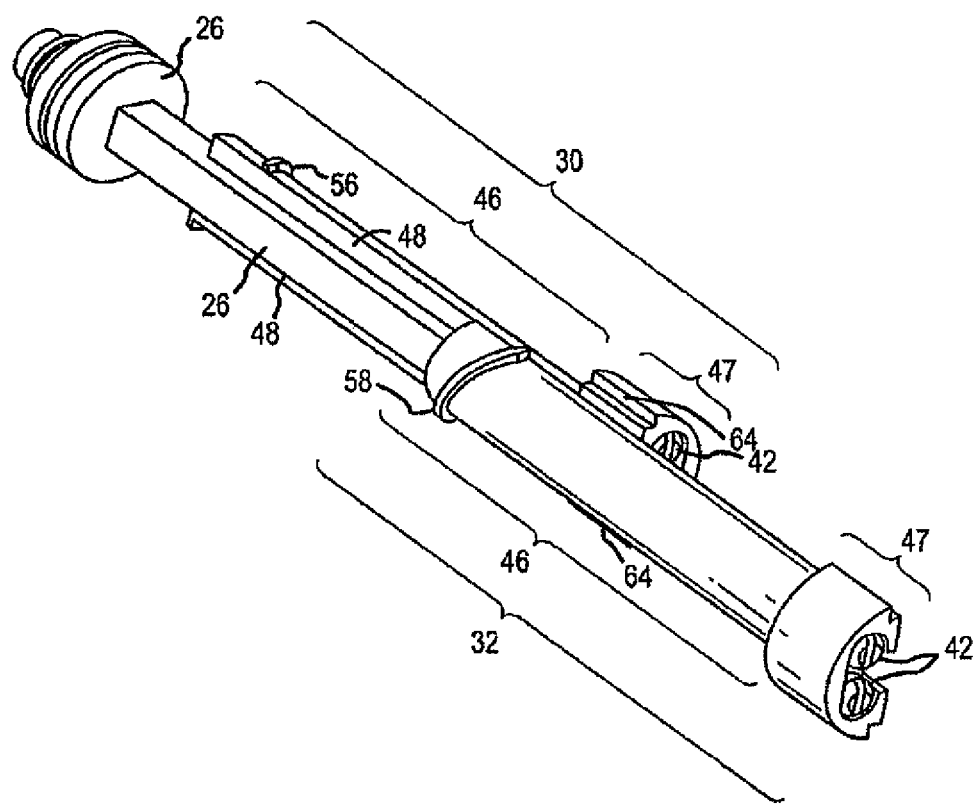
FIG. 13 is a left side isometric view of the slides displaced about the wire guide.

As indicated in FIG. 10, a right slide 30 and a left slide 32 are longitudinally displaceable within the handle 2 and about the proximal end of the wire guide 26. As shown in FIGS. 12 and 13, which are, respectively, a right side isometric view of the slides 30, 32 displaced about the wire guide 26 and a left side isometric view of the slides 30, 32 displaced about the wire guide 26 and a left side isometric view of the slides 30, 32 displaces against the slide face 48 of the opposed slide 30, 32 to form a passage 40 through which the proximal end of the wire guide 26 passes as the slides 30, 32 displace about the wire guide 26. As shown in FIG. 10, the passage 40 formed by the channels 40 also provides a pathway along which the deflection wires 38a, 38b (represented by a dashed line in FIG. 10) travel from a proximal portion of the slides 30, 32, through the wire guide 26, and onward to the extreme distal end 14 of the catheter body 4.

As indicated in FIGS. 12 and 13, each slide 30, 32 has a half-cylinder distal portion 46 and a shorter and wider half-cylinder proximal portion 47. The right slide 30 has a right-handed thread 56 on its distal portion 46. Similarly, the left slide 32 has a left-handed thread 58 on its distal portion 46. Thus. As can be understood from FIG. 10, when the knob 10 is rotated in a clockwise direction relative to the handle grip 12, the right handed threads 62 within the knob 10 engage the right handed threads 56 of the right slide 30, and the left handed threads 64 within the knob 10 engage the left handed threads 56 of the left slide 32. As a result, the right slide 30 is distally displaced within the handle 2 and the left slide 32 is proximally displaced within the handle 2. Accordingly, the deflection wire 38a attached to the right slide 30 is pushed (i.e., subjected to a compressive force) and the deflection wire 38b attached to the left slide 32 is pulled (i.e., subjected to a tension force). Conversely, if the knob is rotated counter-clockwise, the opposite displacement of the slides 30, 32 and deflection wires 38a, 38b will occur.

As indicated in FIG. 10, each deflection wire 38a, 38b is attached to the proximal portion 47 of its respective slide 30, 32 via retention screws 42. the retention screws, which are more clearly illustrated in FIGS. 12 and 13 are threadably mounted in the proximal portions 47.

As shown in FIGS. 12 and 13, each half-cylindrical proximal portion 47 of a slide 30, 32 has an upper and lower planar notch 64 adjacent their respective planar slide faces 47. The function of these notches 64 may be understood by referring to FIGS. 14 and 15.

Figure 14:
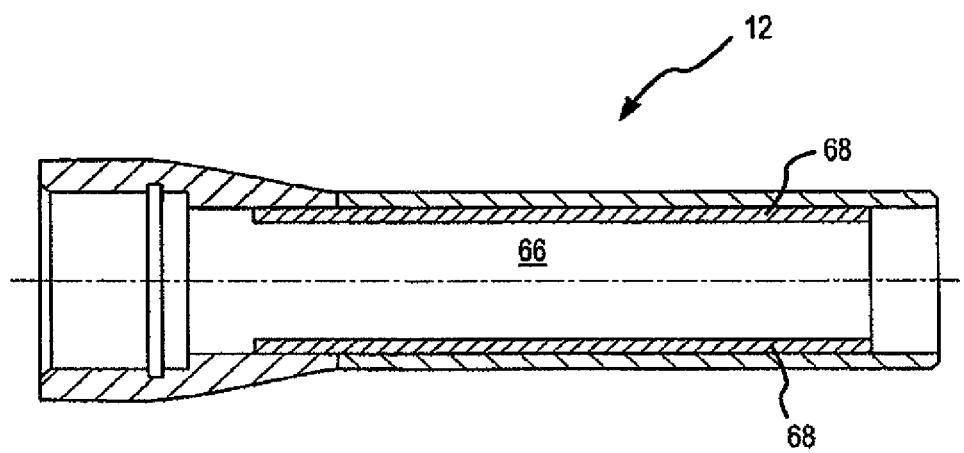
FIG. 14 is a longitudinal sectional elevation of the handle grip taken along section line CC in FIG. 7.
Figure 15:
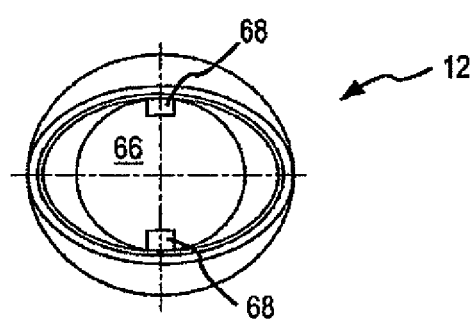
FIG. 15 is a latitudinal sectional elevation of the handle grip taken along section line DD in FIG. 8.

FIG. 14 is a longitudinal section elevation of the handle grip 12 taken along section line CC in FIG. 7. FIG. 15 is a latitudinal section elevation of the handle grip 12 taken along section line DD in FIG. 8. As shown in FIGS. 14 and 15, the handle grip 12 is one integral piece having an interior cylindrical void 66 in which the proximal portions 47 of the slides 30, 32 may displace as indicated in FIG. 10.

As shown in FIGS. 14 and 15, upper and lower ribs 68 extend from the walls that form the interior cylindrical void 66. the ribs 68 run longitudinally along a substantial portion of the cylindrical void's length. As can be understood from FIGS. 12-15, the upper planar notches 64 on the proximal portions 47 of the slides 30, 32 interface with, and displace along, the upper rib 68 as the slides 30, 32 displace within the cylindrical void 66. Similarly, the lower planar notches 64 on the proximal portions 47 of the slides 30, 32 interface with, and displace along, the lower rib 68 as the slides 30, 32 displace within the cylindrical void 66. Thus, the ribs 68 act as thrust surfaces for the slides 30, 32.

Figure 16:
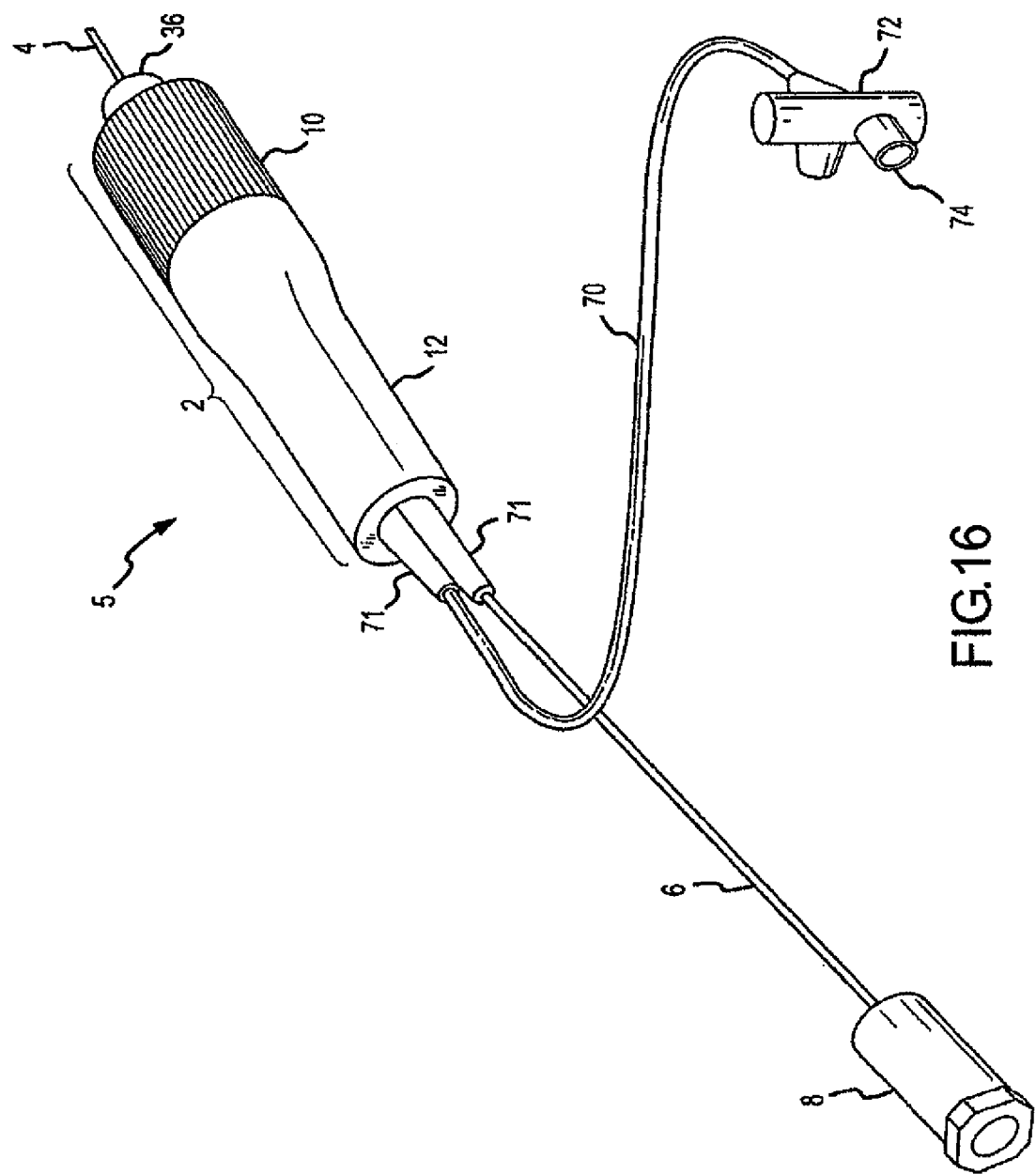
FIG. 16 is an isometric view of the distal end of a control handle for a catheter wherein the handle has a through lumen.

For a detailed discussion of another embodiment of the handle 2 depicted in FIGS. 7-15, reference is now made to FIG. 16. FIG. 16 is an isometric view of the distal end of a control handle 2 for a catheter 5 wherein the handle 2 and catheter body 4 have a through lumen 70. As shown in FIG. 16, in one embodiment, the lumen 70 and the electrical wire tube 6, which extends to the electrical connector 8, pass through strain reliefs 71 and into the proximal end of the handle grip 12. in one embodiment, the lumen 70 terminates at its proximal end with a stopcock 72. In one embodiment, the stopcock 72 has a hemostasis seal 74 that can be utilized for guide wire insertion. While a long flexible length of lumen 70, as depicted in FIG. 16, provides motion isolation while inserting contrast from a syringe, in one embodiment, the lumen 70 does not extend from the handle grip 12. Instead, the stopcock 72 or luer fitting is simply attached to the lumen 70 where it exits the proximal end of the handle grip 12.

Figure 17:
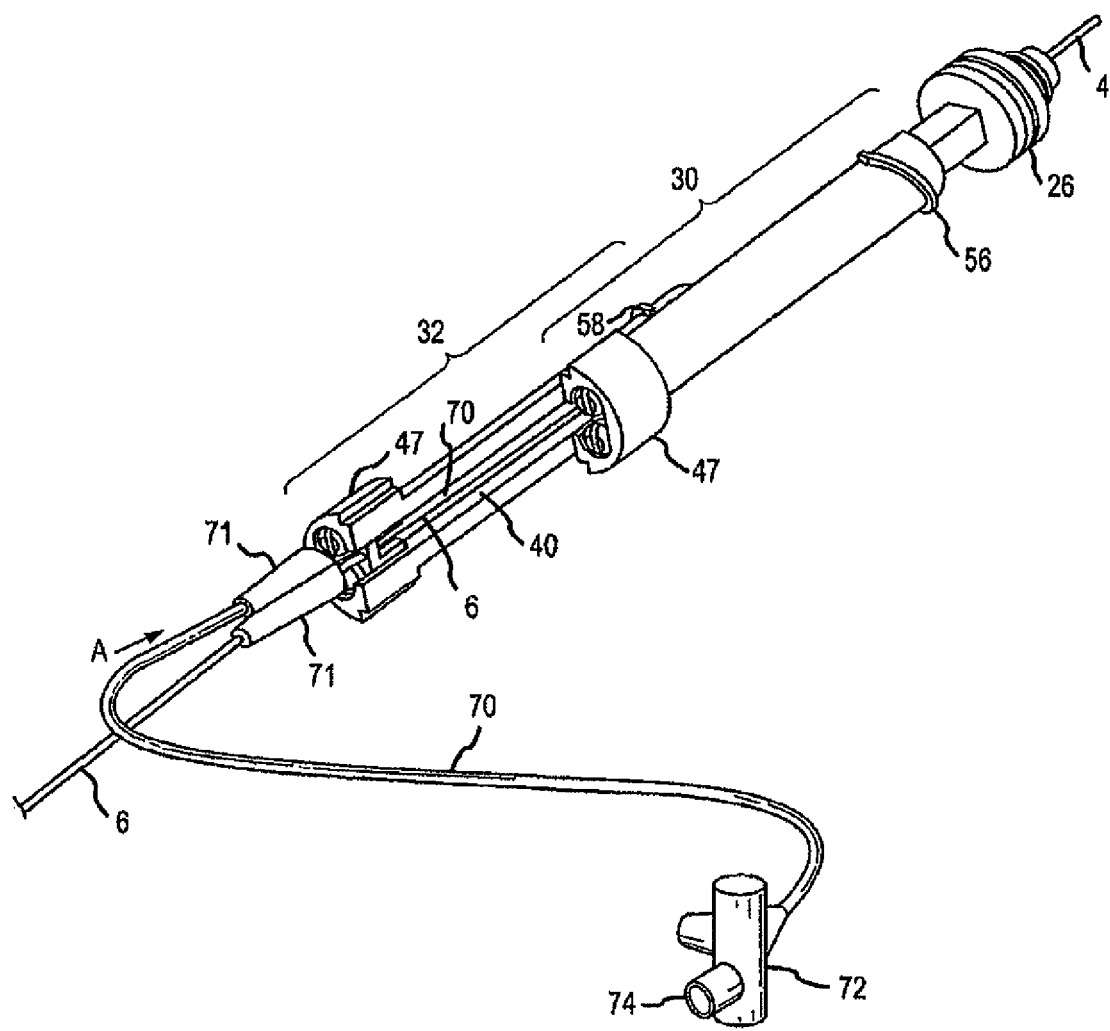
FIG. 17 is an isometric view of the slides, the wire guide, the wire tubing, and the lumen illustrating the path the lumen takes through the handle.
Figure 18:
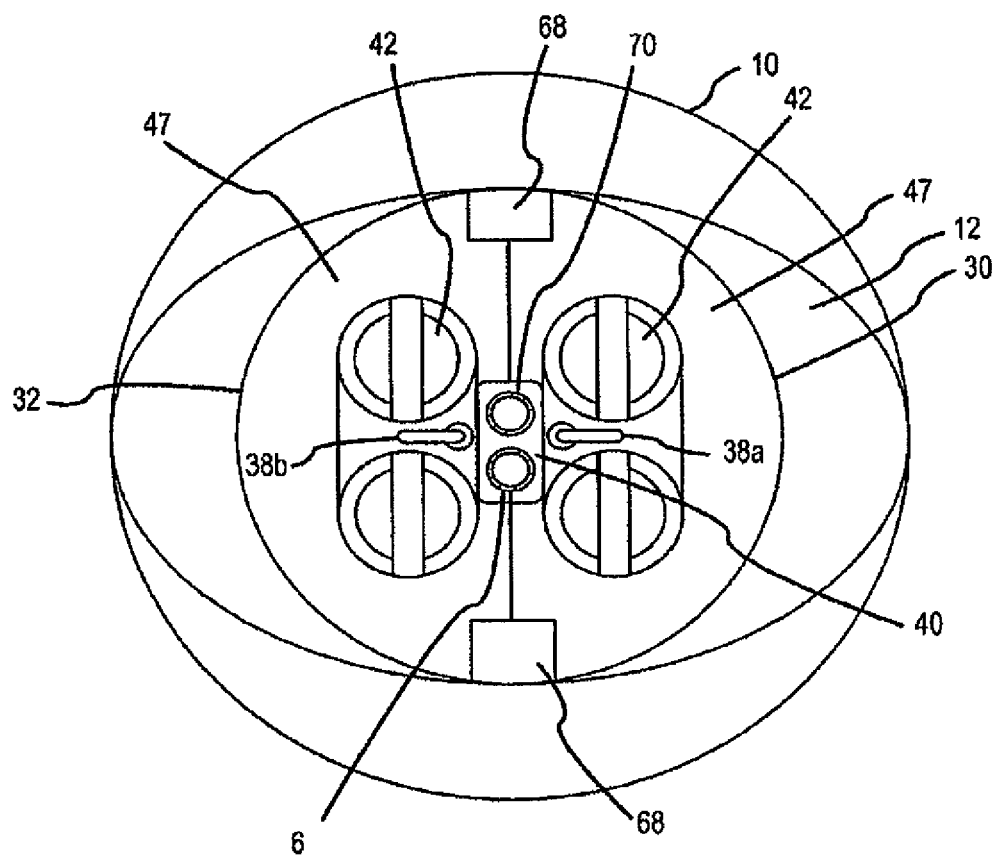
FIG. 18 is an elevation view of the extreme proximal end surfaces of the slides as viewed from arrow A in FIG. 17 and illustrating the path the lumen and wire tubing take into the passage formed by the channels of the slides.
Figure 19:
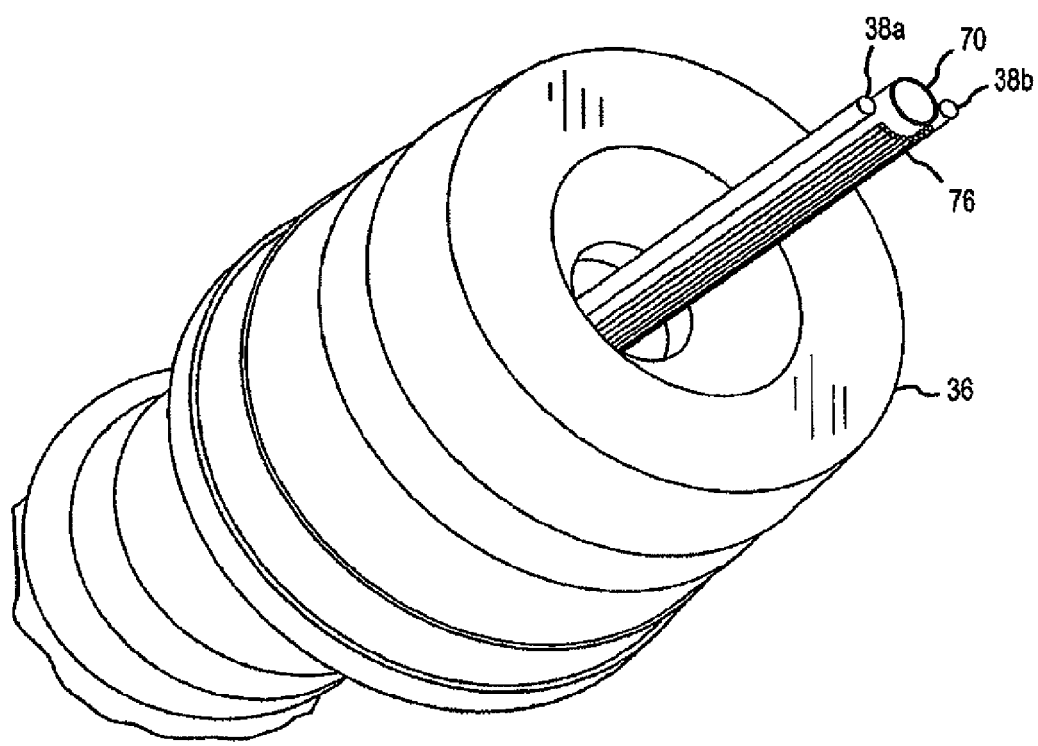
FIG. 19 is an isometric view of the lumen, deflection wires, and electrical wires of the tube exiting the catheter body-retaining nut on the distal end of the handle.

For a better understanding of the path of the lumen 70, reference is now made to FIGS. 17, 18, and 19. FIG. 17 is an isometric view of the slides 30, 32, the wire guide 26, the wire tubing 6, and the lumen 70 illustrating the path the lumen 70 takes through the handle 2. FIG. 18 is an elevation view of the extreme proximal end surfaces of the slides 30, 32 as viewed from arrow A in FIG. 17 and illustrating the path the lumen 70 and wire tubing 6 take into the passage 40 formed by the channels 40 of the slides 30, 32. FIG. 19 is an isometric view of the lumen 70, deflection wires 38a, 38b, and electrical wires 76 of the wire tube 6 exiting the catheter body-retaining nut 36 on the distal end of the handle 2.

As shown in FIGS. 17 and 18, the lumen 70 and the wire tubing 6 pass through their respective reliefs 71 and into the passage 40 formed by the channels 40 in each slide 30, 32. In one embodiment, soon after the wire tubing 6 and the lumen 70 enter the passage 40, the wires 76 of the wire tubing 6 exit the wire tubing 6 and are dispersed about the outer circumference of the lumen 70 as depicted in FIG. 19.

As illustrated in FIG. 17, in another embodiment, after the wire tube 6 and lumen 70 enter the passage 40, the wire tube 6 and the lumen 70 continue on their pathway to the distal end 14 of the catheter body 4 by passing, in a side-by-side arrangement, through the remainder of the passage 40 formed into the slides 30, 32 and into an internal passage that extends along the longitudinal axis of the wire guide 26. near the end of the wire guide 26, the wire 76 exits the wire tube 6. The wire 76, lumen 70 and deflection wires 38a, 38b then pass into the catheter by exiting the catheter body-retaining nut 36 of the handle as indicated in FIG. 19.

Figure 20:
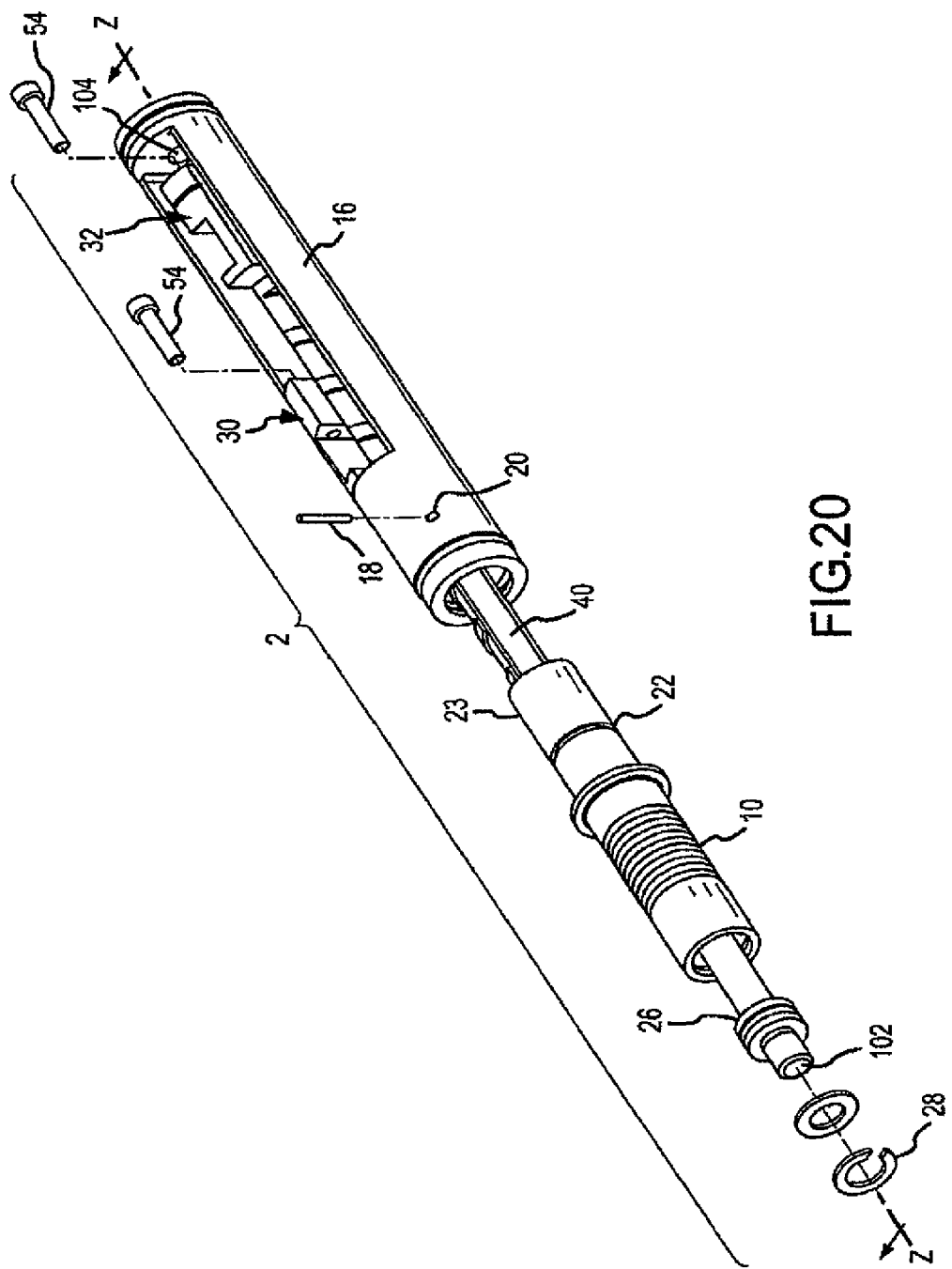
FIG. 20 is an isometric view of another embodiment of the handle exploded to show its various components.

For a detailed discussion of another embodiment of the handle 2, reference is now made to FIG. 20, which is an isometric view of the handle 2 exploded to show its various components. As can be understood from FIG. 20, the features of the handle 2 depicted in FIG. 20 is configured to have a relatively large, generally uniform in diameter, pathway extend the full length of the handle 2 (i.e., from the distal opening 102 in the wire guide 26, through the passage 40 defined in the slides 30, 32 and through an exit hole 104 in the proximal end of the shaft 16).

Figure 21:
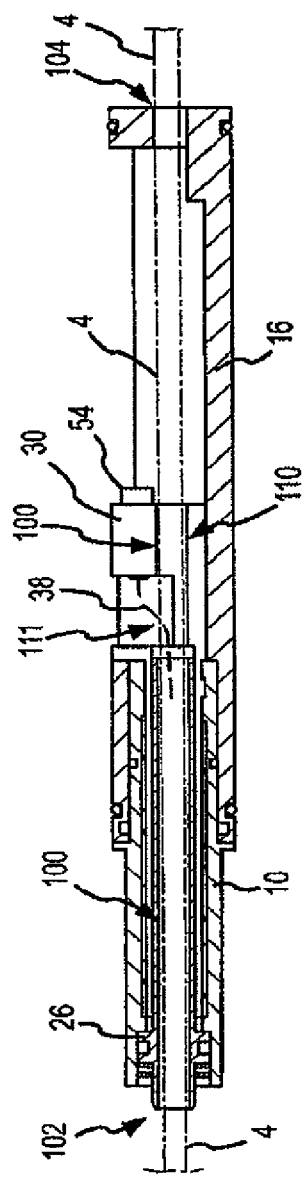
FIG. 21 is a longitudinal sectional elevation taken along section line ZZ in FIG. 20.

The configuration of the handle 2 that allows a relatively large generally uniform in diameter pathway to pass through the length of the handle 2, as depicted in FIG. 20, is more clearly shown in FIG. 21, which is a longitudinal sectional elevation taken along section line ZZ in FIG. 20. As illustrated in FIG. 21, in one embodiment, the pathway 100, which includes the passage through the wire guide 26 and the passage 40 through the slides 30, 32, is large enough that the catheter body 4 itself may pass through the pathway 100 and be connected to the proximal end of the shaft 16 at the exit hole 104. Thus, in one embodiment, to prevent the catheter body 4 from rotating with the adjusting knob 10, the catheter body 4 is affixed to the shaft 16 at the exit hole 104. In one embodiment, the catheter body 4 runs the full length of the handle 4 as depicted in FIG. 21, except the body 4 is affixed to the wire guide 26 at or near the distal opening 102. In other embodiments, the catheter body 4 is affixed to both the wire guide 26 at or near the distal opening 102 and the shaft 16 at the exit hole 104.

Figure 22:
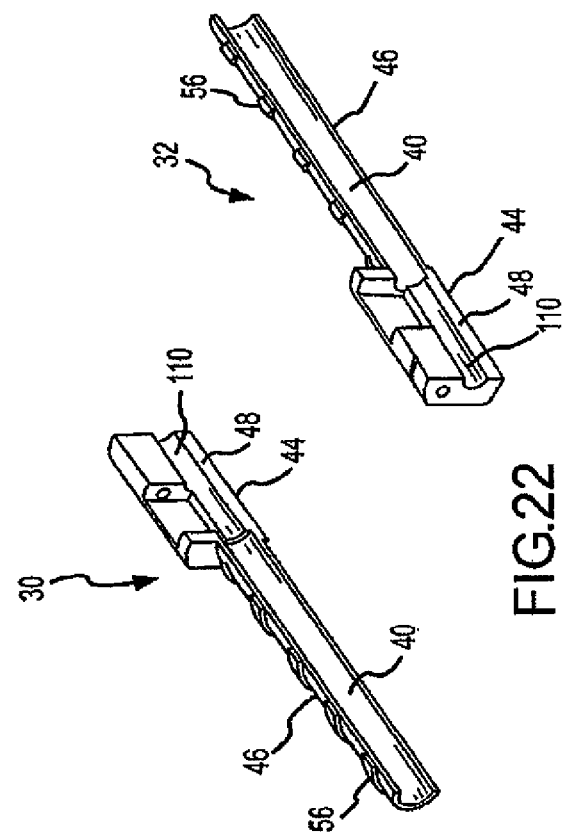
FIG. 22 are isometric views of the slides oriented to show their respective portions of the passage and their planar slide faces.

As can be understood from FIG. 21 and as more clearly depicted in FIG. 22, which is isometric views of the slides 30, 32 oriented to show their portions of the passage 40 and their planar slide faces 48, the passage 40 is large enough in diameter to displace over the outer diameter of the wire guide 26. As shown in FIGS. 21 and 22, a catheter body passage 110 passes through the proximal portion 44 of each slide 30, 32, thereby allowing the slides 30, 32 to displace back and forth over the outer surface of the catheter body 4.

As indicated in FIG. 21, in one embodiment, the catheter body 4 has an opening 111 in its wall that allows the wires 38 to exit the body 4 and connect to the slides 30, 32. In one embodiment, the wires 38 connect to the slides 30, 32 via tension adjustments screws 54 as previously discussed.

Due to the configuration of the slides 30, 32, the wire guide 26 and the shaft 16, the catheter body 4 may run uninterrupted the full length of the handle 2. As a result, electrical wiring 76 (see FIG. 19) and a lumen 70 may be routed the full length of the handle 2 by way of the body 4.

Figure 23:
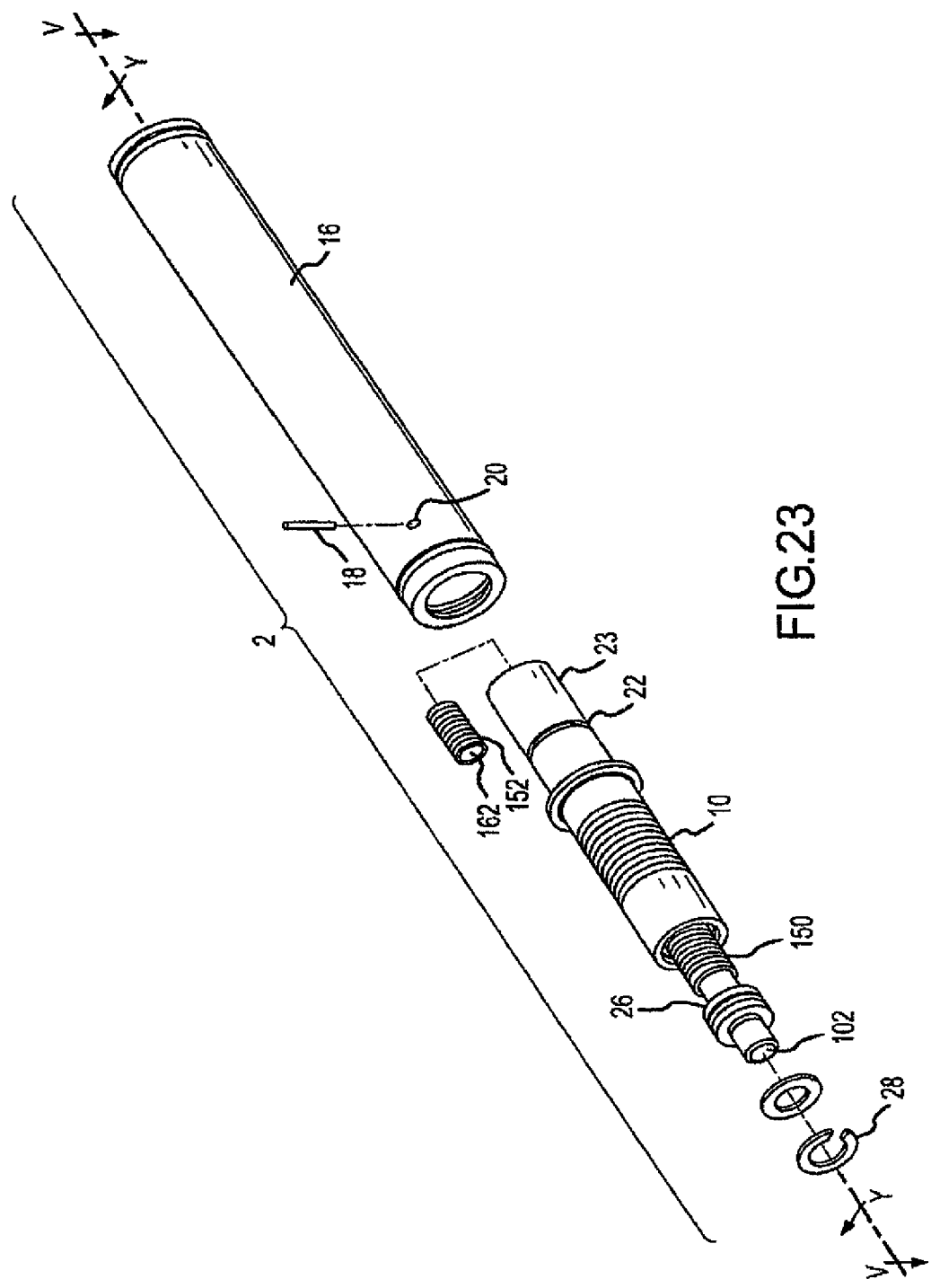
FIG. 23 is an isometric view of another embodiment of the handle exploded to show its various components.
Figure 24:
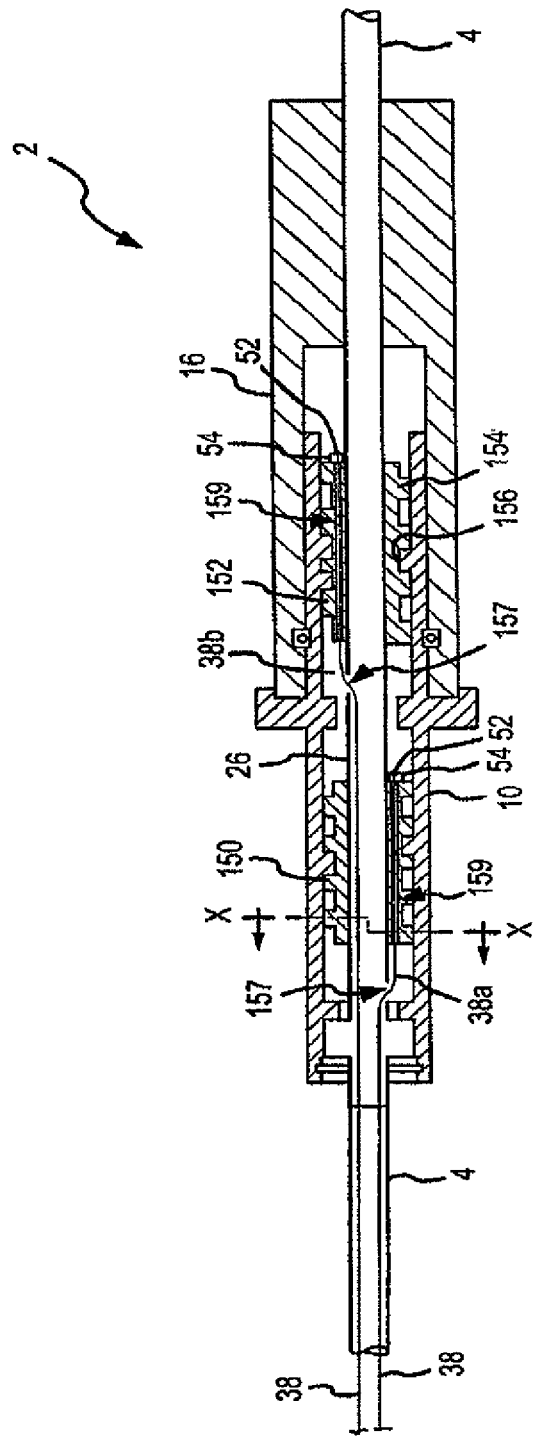
FIG. 24 is a longitudinal sectional elevation of the handle taken along section line YY of FIG. 23.

For a detailed discussion of another embodiment of the handle 2 of the present invention, reference is now made to FIGS. 23 and 24. FIG. 23 is an isometric view of the handle 2 exploded to show its various components. FIG. 24 is a longitudinal sectional elevation of the handle 2 taken along section line YY of FIG. 23. Generally speaking, the features of the handle 2 depicted in FIGS. 23 and 24 are similar to the features of the handle depicted in FIG. 20, except the two embodiments employ different slider arrangements. For example, the embodiments depicted in FIGS. 1-22 employ parallel slides or members 30, 32 (i.e., the slides 30, 32 exist within the handle 2 in a parallel or side-by-side arrangement). As will be understood from FIGS. 23 and 24 and the following figures, in the embodiment of the handle 2 depicted in FIGS. 23 and 24, the slides or members 150, 152 exist within the adjustment knob 10 in a series arrangement (i.e., the slides 150, 152 are not parallel or side-by-side to each other, but are oriented end-to-end along a longitudinal axis of the handle 2).

As shown in FIGS. 23 and 24, the adjusting knob 10 is pivotally coupled to the distal end of the mounting shaft (i.e., base portion) 16. The wire guide 26 extends through the center of the adjusting knob 10 and the mounting shaft 16. The catheter body 4 is coupled to the distal end of the wire guide 26 and, in one embodiment, extends through the wire guide 26 and out of the proximal end of the mounting shaft 16.

As shown in FIGS. 23 and 24, a distal slide 150 is located in a distal portion of the adjusting knob 10, and a proximal slide 152 is located in a proximal portion (i.e., hub portion 23) of the adjusting knob 10. As illustrated in FIG. 24, the outer surface of each slide 150, 152 has threads 154 that mate with threads 156 on an interior surface of the adjusting knob 10.

As illustrated in FIG. 24, each deflection wire 38a, 38b travels along the interior of the wire guide 26 until it exits the wire guide 26 at a hole 157 in the sidewall of the wire guide 26. Each deflection wire 38a, 38b then extends to the slide 150, 152, to which the deflection wire 38a, 38b is attached. In one embodiment, in order to attach to a slide 150, 152, a deflection wire 38a, 38b passes through a passage 159 in the slide 150, 152 and attaches to a hollow tension adjustment screw 54 via a knot 52 as previously described in the Detailed Description.

Figure 25:
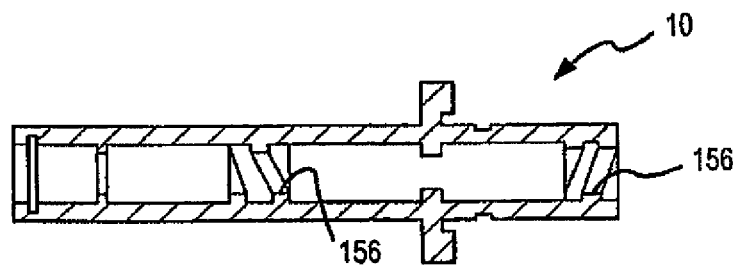
FIG. 25 is the same longitudinal sectional elevation of the adjusting knob as depicted in FIG. 24, except the adjusting knob is shown by itself.
Figure 26:
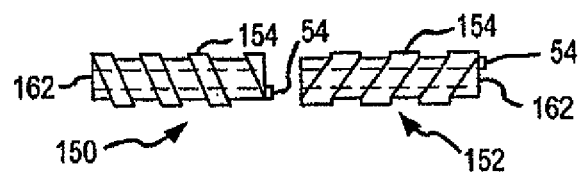
FIG. 26 is a side elevation of the slides.

For a better understanding of the orientation of the threads 154, 156, reference is now made to FIGS. 25 and 16. FIG. 25 is the same longitudinal sectional elevation of the adjusting knob 10 as it is depicted in FIG. 24, except the adjusting knob 10 is shown by itself. FIG. 26 is a side elevation of the slides 150, 152.

As shown in FIGS. 25 and 26, in one embodiment, the distal slide 150 has right hand threads 154 that engage right hand threads 156 in the distal portion of the adjusting knob 10, and the proximal slide 152 has left hand threads 154 that engage the left hand threads 156 in the proximal portion of the adjusting knob 10. Thus, as can be understood from FIGS. 23-26, when the adjusting knob 10 is relative to the mounting shaft 16 in a first direction about the longitudinal axis of the handle 2, the slides 150, 152 will converge along the wire guide 26, thereby causing the first wire 38 to be placed into tension and the second wire 38 to be compressed. As a result, the distal end 14 of the catheter body 4 will deflect in a first direction. Similarly, when the adjusting knob 10 is rotated in a second direction that is opposite from the first direction, the slides 150, 152 will diverge along the wire guide 26, thereby causing the first wire 38 to be compressed and the second wire 38 to be placed into tension. As a result, the distal end 14 of the catheter body 4 will deflect in a second direction generally opposite from the first direction.

Figures 27A, 27B:
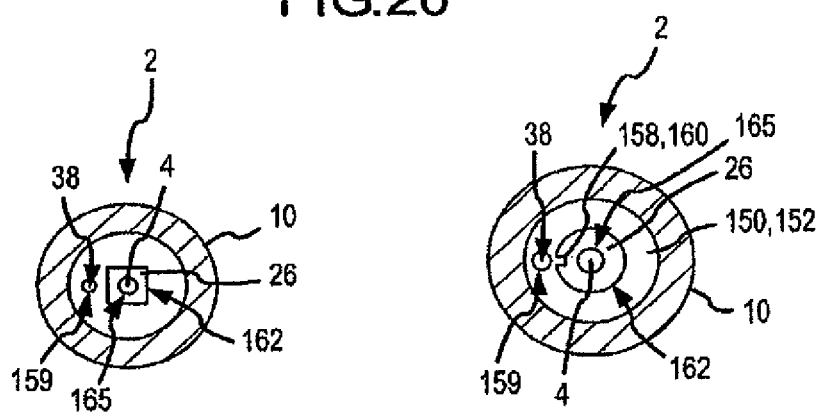
FIG. 27A is a latitudinal section elevation of the handle, as taken along section line XX in FIG. 24, wherein the wire guide has a square cross section.
FIG. 27B is the same latitudinal sectional elevation depicted in FIG. 27A, except the wire guide has a circular cross section and a key/groove arrangement.

In one embodiment, to prevent the slides 150, 152 from simply rotating around the wire guide 26 when the adjusting knob 10 is rotated, the slides 150, 152 and wire guide 26 are configured such that the slides 150, 152 will displace along the wire guide 16, but not rotationally around it. For example, as indicated in FIG. 27A, which is a latitudinal sectional elevation of the handle 2 as taken along section line XX in FIG. 24, the wire guide 26 has a square cross section that mates with a square hole 162 running the length of the slide, 150, 152. The interaction between the square hole 162 and the square cross section of the wire guide 26 prevents a slide 150, 152 from rotating about the wire guide 26, but still allows the slide 150, 152 to displace along the length of the wire guide 26.

Figure 28:
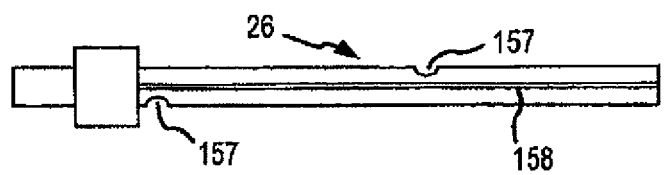
FIG. 28 is a side elevation of one embodiment of the wire guide equipped with a groove.

In another embodiment, as shown in FIG. 27B, which is the same latitudinal sectional elevation depicted in FIG. 27A, each slide 150, 152 has a hole 162 with a circular cross section. Each hole 162 runs the length of its respective slide 150, 152 and includes a key 160 that extends into hole 162 from the interior circumferential surface of the hole 160. The key 160 engages a groove or slot 158 that runs along the length of the wire guide 26 as depicted in FIG. 28, which is a side elevation of one embodiment of the wire guide 26. The interaction between the key 160 and the slot 158 prevents a slide 150, 152 from rotating about the wire guide 26, but still allows the slide 150, 152 to displace along the length of the wire guide 26.

As shown in FIGS. 27A and 27B, a hollow shaft 165 extends through the wire guide 26. This allows a catheter body 4 with a lumen to extend completely through the handle 2 as shown in FIG. 24.

For a detailed discussion of another embodiment of the handle 2 that is similar to the embodiment depicted in FIG. 23, reference is now made to FIGS. 29 and 30. FIG. 29 is a longitudinal sectional elevation of the handle 2 as if taken through section line VV in FIG. 23 and wherein section line VV forms a plane that is perpendicular to the plane formed by section line YY in FIG. 23.

As illustrated in FIGS. 29 and 30, the handle 2 includes an adjusting knob 10 pivotally coupled to the distal end of the mounting shaft (i.e., base portion) 16. In one embodiment, the adjusting knob 10 includes a proximal end 170, a distal end 172 and a threaded shaft 173, which is connected to the proximal end 170 and extends distally along the longitudinal axis of the adjusting knob 10. The threaded shaft 173 includes a distal end 174, a proximal end 176, a series of right hand threads 178 along a distal portion of the shaft 173, and a series of left hand threads 180 along a proximal portion of the shaft 173.

As shown in FIGS. 29 and 30, a distal slide 150 is located in a distal portion of the adjusting knob 10, and a proximal slide 152 is located in a proximal portion (i.e., hub portion 23) of the adjusting knob 10. Each slide has a hole 155 through which the threaded shaft 173 passes. The inner circumferential surface of the hole 155 for the distal slide 150 has right hand threads that mate with the right hand threads 178 on the distal portion of the shaft 173. Similarly, the inner circumferential surface of the hole 155 for the proximal slide 152 has left hand threads that mate with the left hand threads 180 on the proximal portion of the shaft 173. In other embodiments, the locations for the left and right threads are reversed.

As can be understood from FIGS. 29, 30, and 31, which is an isometric view of one embodiment of the wire guide 26, a hollow center shaft 182 extends from the distal end of the wire guide 26, through the threaded shaft 173 of the adjustment knob 10, and to the proximal end of the base shaft 16. Thus in one embodiment, a catheter body 4 may be routed through the lumen 165 of the wire guide's hollow center shaft 182 to exit the proximal end of the handle 2, as illustrated in FIGS. 29 and 30.

As illustrated in FIG. 29, each deflection wire 38a, 38b travels along the interior of the wire guide 26 until it exits the wire guide 26 at a hole 157 in the sidewall of the wire guide 26. Each deflection wire 38a, 38b then extends to the slide 150, 152 to which the deflection wire 38a, 38b is attached. In one embodiment, in order to attach to a slide 150, 152, a deflection wire 38a, 38b passes through a passage 159 in the slide 150, 152 and attaches to a hollow tension adjustment screw 54 via a knot 52 as previously described in the Detailed Description.

In one embodiment, as shown in FIG. 29, the deflection wire 38b leading to the proximal slide 152 passes through a second passage 161 in the distal slide 150. The second passage 161 has sufficient clearance that the passage 161 may easily displace along the wire 38b when the distal slide 150 displaces distally and proximally. The second passage 161 serves as a guide that stiffens the wire 38b and helps to reduce the likelihood that the wire 38b will bend when compressed.

As can be understood from FIGS. 29 and 30, when the adjusting knob 10 is rotated relative to the mounting shaft 16 in a first direction about the longitudinal axis of the handle 2, the slides 150, 152 will converge along the threaded shaft 173, thereby causing the first wire 38a to be placed into tension and the second wire 38b to be compressed. As a result, the distal end 14 of the catheter body 4 will deflect in a first direction. Similarly, when the adjusting knob 10 is rotated in a second direction that is opposite from the first direction, the slides 150, 152 will diverge along the threaded shaft 173, thereby causing the first wire 38a to be compressed and the second wire 38b to be placed into tension. As a result, the distal end 14 of the catheter body 4 will deflect in a second direction generally opposite from the first direction.

In one embodiment, to prevent the slides 150, 152 from simply rotating with the threaded shaft 173 within the adjusting knob 10 when the adjusting knob 10 is rotated, the slides 150, 152 and wire guide 26 are configured such that the slides 150, 152 will displace along the threaded shaft 173, but not rotationally within the adjusting knob 10. For example, as indicated in FIGS. 31 and 32, which is a latitudinal sectional elevation of the handle 2 as taken along section line WW in FIG. 29, the wire guide 26 has right and left semicircular portions 190 that oppose each other and extend along the length of the hollow center shaft 182 of the wire guide 26. As shown in FIG. 32, the generally planar opposed faces 192 of the semicircular portions 190 abut against the generally planar side faces 194 of the slides 150, 152. This interaction prevents a slide 150, 152 from rotating within the adjustment knob 10 when the knob 10 is rotated, but still allows the slide 150, 152 to displace along the length of the threaded shaft 173.

In an another embodiment, the handle 2 allows a user to manipulate the extreme distal end 14 of a catheter body 4 having a lumen extending completely therethrough in a bi-directional manner by pivoting a first adjusting knob 10a relative to handle grip 12 in one direction or the other about the longitudinal axis of the handle 2, and allows the user to rotate an instrument catheter 196 disposed within the lumen of the catheter body 4 by pivoting a second adjusting knob 10b relative to the handle grip 12 about the longitudinal axis of handle 2. For clarity, the instrument catheter 196 will be referred to as an ultrasound catheter, but the instrument catheter 196 may also be a therapeutic catheter, such as an ablation catheter, or another type of diagnostic catheter without departing from the spirit and scope of the invention. The ultrasound catheter 196 is disposed in a coaxial relationship within the lumen of the catheter body 4 allowing a the bidirectional manipulation of the catheter 5 to cause a corresponding deflection in the ultrasound catheter 196. In this manner, catheter 5 acts as a guiding catheter for the ultrasound catheter 196 and allows a user to steer the ultrasound catheter 196 by deflecting the guiding catheter 5.

Now referring the FIGS. 36-40, the adjusting knob 10a is pivotally attached to mounting shaft 16 contained within handle grip 12. The adjusting knob 10a is attached to mounting shaft 16 with a dowel pin 18 that is inserted into a pinhole 20a in the distal end of the shaft 16 that mates with a groove 22 in a hub portion 23 of the knob 10a. The groove 22 allows adjusting knob 10a to pivot freely around the longitudinal axis of mounting shaft 16 while contact between the walls of groove 22 and dowel pin 18 constrain adjusting knob 10a from moving axially along the longitudinal axis of mounting shaft 16. A right slide 30 and a left slide 32 are positioned within slot 34 of the mounting shaft 16.

Figure 36:
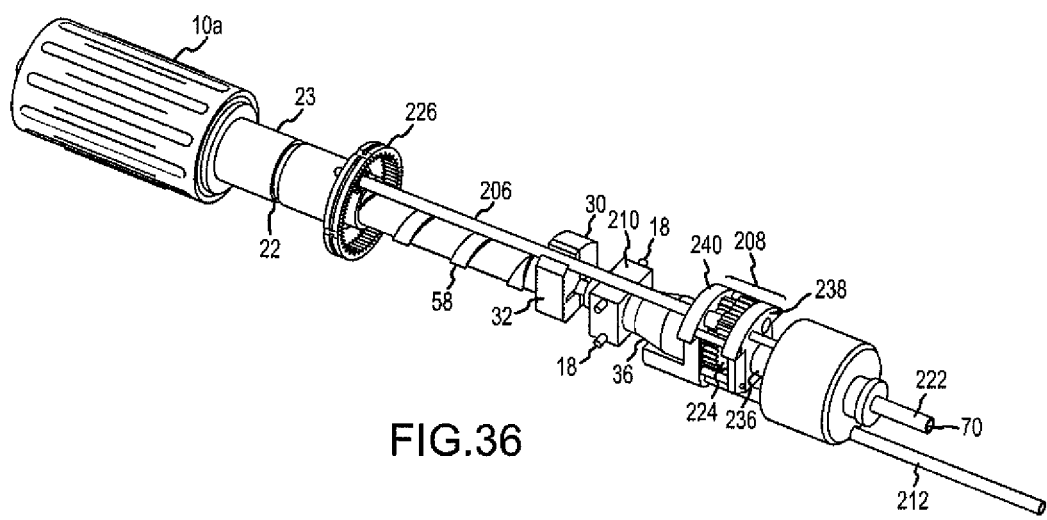
FIG. 36 an isometric view of an embodiment of the handle having a first adjustment knob and a second adjustment knob.
Figure 37:
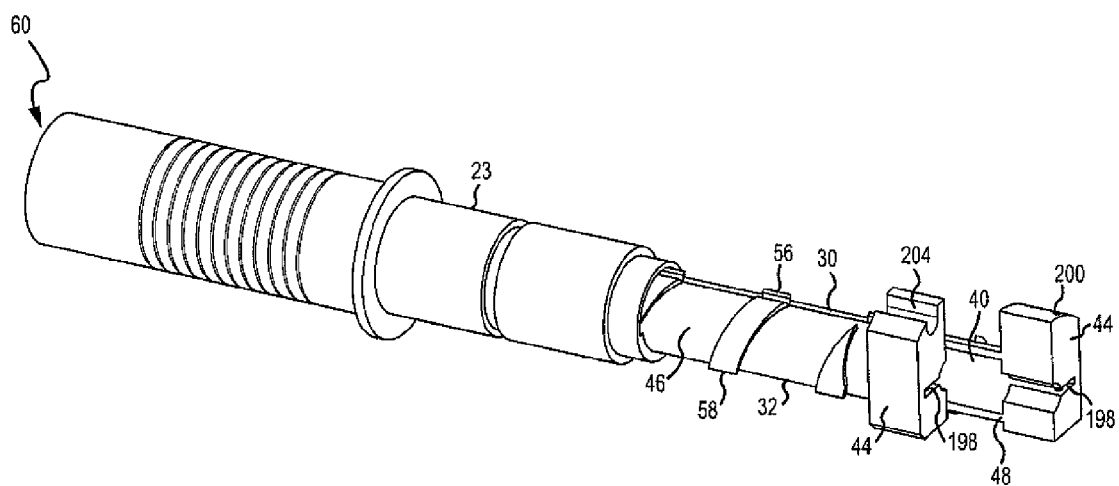
FIG. 37 is an isometric view of the handle of FIG. 36 illustrating the relationship of the first adjusting knob to the deflection members.

Now referring to FIGS. 36 and 37, slides 30, 32 have a generally rectangular box-like proximal portion 44 and a half-cylinder distal portion 46. Each proximal portion 44 has a generally planar sides that contact the walls of slot 34.

Each slide 30, 32 has a planar face 48 extending from the distal portion 46 to the proximal portion 44 that is meant to slideably abut against the planar face 48 of the opposing slide 30, 32. The planar face 48 of each slide 30, 32 is hollowed out along its longitudinal axis to form a passage 40 through which the guiding catheter 5 and its deflection wires 38a, 38b as well as the ultrasound catheter 196 pass. The proximal portion 44 of slides 30, 32 have a slot 198 through which deflection wires 38a, 38b pass. The defection wires 38a, 38b are retained in slot 198 using a dowel pin (not shown) inserted in hole 200, and deflection wires 38a, 38b are constrained axially by a wire lock nut (not shown) attached, for example, by soldering to deflection wires 38a, 38b. The proximal portion of the left slide 32 contains a notch 204 that allows a drive shaft 206 to extend from the proximal end of the slot 34 distally to the second adjusting knob 10b. In an alternative embodiment, the right slide 30 can contain a notch 204 to allow a drive shaft 206 to extend from the proximal end of the slot 34 distally to the second adjusting knob 10b.

The outer circumference of the distal portion 46 of right slide 30 is threaded with a right-hand thread 56, and the outer circumference of the half-cylinder distal portion 46 of the left slide 32 is threaded with a left-hand thread 58. In another embodiment, the outer circumference of the half-cylinder distal portion 46 of the right slide is threaded with a left-hand thread 58, and the outer circumference of the half-cylinder distal portion 46 of the left slide 32 is threaded with a right-hand thread. When assembled in handle 2 the planar face 48 of each of the slides 30, 32 abut and form a cylinder having right-hand thread 56 on one half of the outer surface of cylinder and left-hand thread 58 on the other half of the outer surface of the cylinder.

Now referring to FIGS. 36-39, the relationship of slides 30, 32 to adjusting knob 10a will be described. Adjusting knob 10a contains a shaft 60 extending from the proximal end of hub 23 to the distal end of adjusting knob 10a through which guiding catheter 5 and ultrasound catheter 196 pass. A portion of shaft 60 is threaded with an internal right-hand thread and the same portion of shaft 60 is also threaded with an internal left-hand thread (not shown). The internal threads of the shaft 60 engage with threads 56, 58 of the slides 30, 32. Thus, when the adjusting knob 10a is rotated the internal and external right-hand threads 56 engage and the internal and external threads 58 engage and cause simultaneous opposed displacement of the right and left slides 30, 32 longitudinally within slot 34. The proximal portions 44 of each of slide 30, 32 engages slot 34 so as to prevent slides 30, 32 from rotating with adjusting knob 10a.

The movement of slides 30, 32 in opposite directions through the pivoting of adjusting knob 10*a* causes the deflection wires 38*a*, 38*b* to be placed in a state of tension or compression. For example, when right slide 30 is disposed in a proximal direction in response to the pivoting of adjusting knob 10*a* the deflection wire 38*a* attached to the right slide 30 is pulled in a proximal direction causing wire 38*a* to be placed in tension. Simultaneously, left slide 32 is disposed in a distal direction in response to the pivoting of adjusting knob 10*a* and deflection wire 38*b* attached to the left slide 32 is pushed in a distal direction causing the wire 38*b* to be placed in compression. When adjusting knob 10*a* is pivoted in the opposite direction, right slide 30 is disposed distally placing deflection wire 38*a* into compression and left slide 32 is simultaneously disposed proximally placing deflection wire 38*b* into tension.

Placing deflection wire 38*a* in tension and deflection wire 38*b* into compression by pivoting adjusting knob 10*a* in a first direction causes the extreme distal end 14 of the guiding catheter 5 to deflect in a first direction. Conversely, placing deflection wire 38*a* in compression an deflection wire 38*b* into tension by pivoting adjusting knob 10*a* in a second direction causes the extreme distal end of the guiding catheter 5 to deflect in a second direction. Guiding catheter 5 extends proximally through the shaft 60 of adjusting knob 10*a*, through passage 40 of slides 30, 32, and terminates in a proximal end having a retaining nut 36. The retaining nut 36 abuts against the distal face of gear assembly 208 and provides a hemostatic seal between the retaining nut 36 and gear assembly 208. guiding catheter 5 is constrained within mounting shaft 16 by pillow block 210. In one embodiment, the retaining nut 36 of guiding catheter 5 is flared such that it has an outer diameter greater than the outer diameter of the catheter body 4. Pillow block 210 can be configured to have an internal surface configured to mate to the flared retaining nut 36. In an alternative embodiment, the retaining nut 36 can have an annular ring extending perpendicular to the longitudinal axis of the guiding catheter 5, which abuts against pillow block 210 to constrain guiding catheter 5 against the gear assembly 208. Pillow block 210 is attached to mounting shaft 16 with dowel pins 18 inserted into pin holes 20*b*, 20*c*.

The retaining nut 36 of guiding catheter 5 may be configured to receive an irrigation lumen 212. The irrigation lumen 212 allows the user to introduce an irrigation fluid into the guiding catheter 5 that prevents body fluids, such as blood, from entering the lumen 70 of the guiding catheter 5. Irrigation fluid delivered through the irrigation lumen 212 provides lubrication between the ultrasound catheter 196 and the guiding catheter's 5 inner wall.

Ultrasound catheter 196 has a distal end 214, a flexible tubular body 216 that may have a lumen extending therethrough, and a proximal end 218. The distal end 214 has an ultrasound element 220 described in further detail below. The ultrasound body 216 extends from the distal end 214 to the gear assembly 208 within the lumen of the guiding catheter 5. The ultrasound body 216 is not connected directly to the guiding catheter 5 and can freely rotate within the lumen. The ultrasound body 216 exits the guiding catheter 5 through its retaining nut 36 and extends into a hemostasis tube 222. The hemostasis tube's 222 distal end is substantially coplanar with the distal face of the gear assembly 208, and extends proximally through the gear assembly 208 to exit handle grip 12 at its proximal end. The hemostasis tube 222 passes through and is fixedly attached to a positioning gear 224 within the gear assembly 208, which causes the hemostasis tube 222 to rotate with the positioning gear 224. Thus, the lumen of the catheter 5 and the hemostasis tube 222 create a continuous lumen 70 extending from the distal tip 14 of the catheter 5 to the proximal end of handle 2.

The portion of the ultrasound body 196 passing through the hemostasis tube 222 is fixedly attached to the hemostasis tube 222 by bonding the inner surface of the hemostasis tube to the outer surface of the ultrasound body 216 using an adhesive, such as a glue or epoxy resin. The bond between the ultrasound body 216 and hemostasis tube 222 causes the ultrasound body, and consequently the ultrasound element 220, to rotate within the lumen of the guiding catheter 5 when the positioning gear 224 is rotated. The bonding also provides a hemostatic seal preventing irrigation fluid introduced into the lumen of guiding catheter 5 from leaking out of the handle 2 through the hemostasis tube 222.

Figure 38:
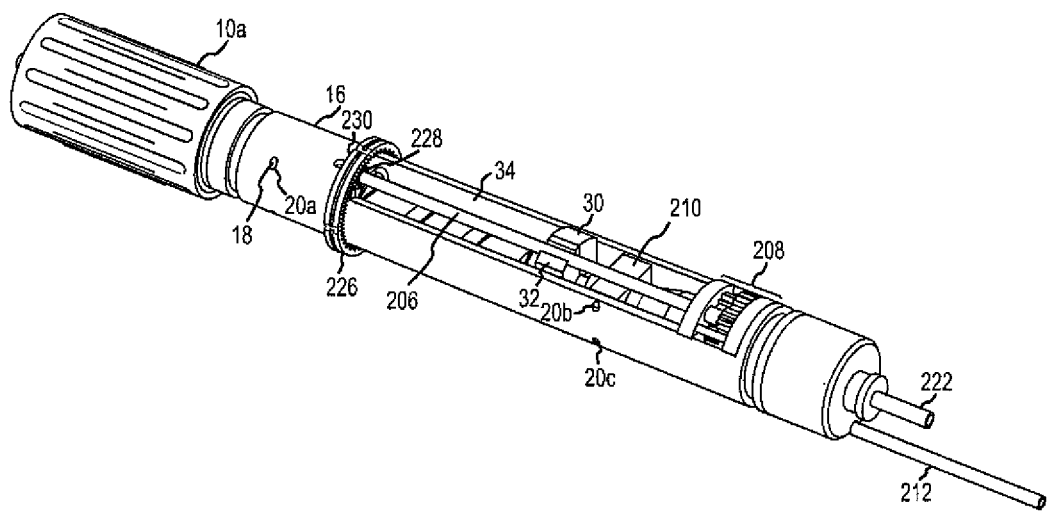
FIG. 38 is an isometric view of an embodiment of the handle having a first adjustment knob and a second adjustment knob illustrating the components of FIG. 36 within a shaft.
Figure 39:
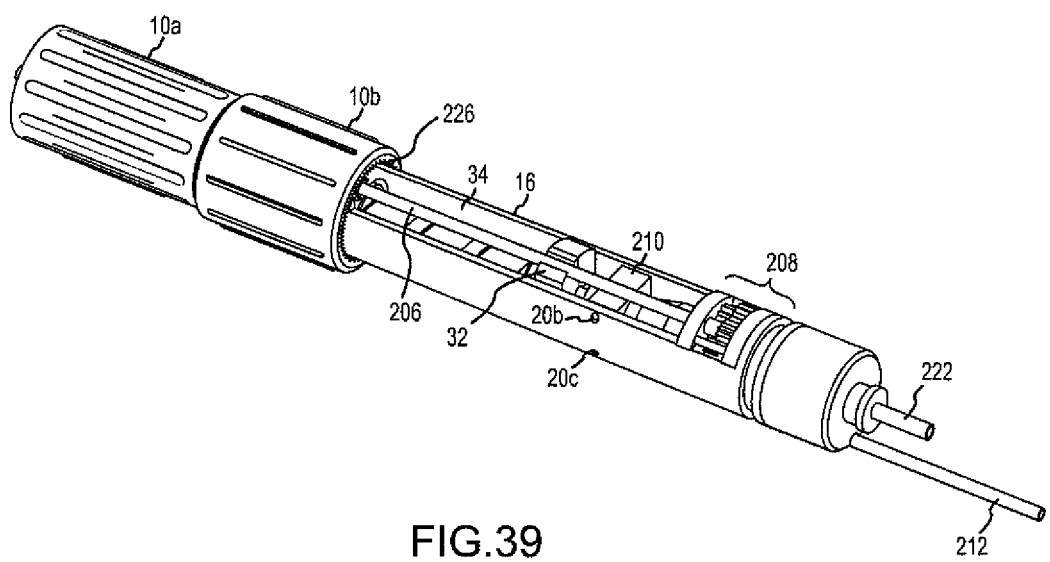
FIG. 39 is an isometric view of the handle of FIG. 39 illustrating the position of the second adjusting knob.
Figure 40:
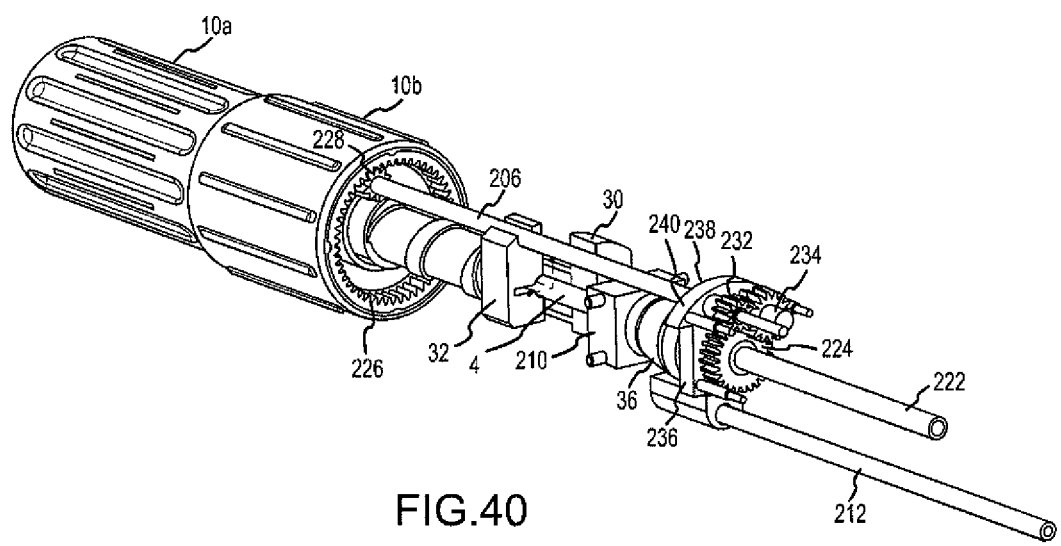
FIG. 40 is an isometric view one embodiment of the handle having a rotation assembly illustrating the relationship between the rotation assembly and the second adjusting knob.

For a more detailed discussion of the relationship between the second adjusting knob 10*b* and the rotation of the ultrasound element 196, reference is now made to FIGS. 38-40. The second adjusting knob 10*b* is positioned proximal to the first adjusting knob 10*a* and distal to handle grip 12, and is thereby constrained along the longitudinal axis of handle 2. The second adjusting knob 10*b* contains an internal gear 226 disposed to engage with a reduction gear 228 contained within handle 2. The reduction gear 228 is attached to the distal end of the drive shaft 206 that exits the gear assembly 208 and extends distally to the second adjustment knob 10*b*. The distal end of the drive shaft 206 is supported within a notch 230 of the mounting shaft 16 to allow torque from the internal gear 226 to be transferred to the reduction gear 228 without detrimental bending that can occur in long cantilevered members. As the second adjustment knob 10*b* is pivoted about the longitudinal axis of the handle 2, the internal gear 226 engages the reduction gear 228 and causes the drive shaft 206 to rotate. The proximal end of the drive shaft 206 extends through the distal face of the gear assembly 208 and is fixedly attached to a drive gear 232 within the gear assembly 208. The gear assembly 208 contains one or more ratio gears 234 disposed to transmit torque from the drive gear 232 to the positioning gear 224 such that the positioning gear rotates when the second adjusting knob 10*b* is pivoted about the longitudinal axis of handle 2.

In one embodiment, the ratio gears 234 are selected to provide a 1:1 gear ratio between rotation of the second adjustment knob 10*b* attached to internal gear 226 and rotation of the positioning gear 224 and the attached ultrasound catheter 196. The number and type of ratio gears 234 may cause the ultrasound catheter 196 to rotate in the same direction as the second adjusting knob 10*b* is pivoted. For example, when adjusting the second adjusting knob 10*b* is pivoted in a counter-clockwise direction, the ratio gears 234 should cause ultrasound catheter 196 to rotate in a counter-clockwise direction by rotating positioning gear 224 in a counter-clockwise direction. And, when the second adjusting knob 10*b* is pivoted in a clockwise direction, the ratio gears should cause the ultrasound catheter 196 to rotate in a clockwise direction by rotating the positioning gear 224 in a clockwise direction. Ensuring that both the ultrasound catheter 196 and knob 10*b* rotate in the same direction allows for more intuitive control of the ultrasound catheter 196 by the user.

A 1:1 ratio of rotational movement between the second adjusting knob 10*b* and the ultrasound catheter 196 allows the user to more easily visualize the orientation of the ultrasound element 220 when the catheter is positioned within a patient. When a 1:1 ratio is used, the facing of the ultrasound element 220 can be further indicated to the user through the use of a raised bump or other tactile feature on adjusting knob 10*b* aligned with the ultrasound element 220 such that the tactile feature is within the ultrasound plane emitted by the ultrasound element 220. The tactile feature allows the user to ascertain the orientation of the ultrasound element 220 by the feel of the tactile feature when gripping the adjusting knob 10*b*.

The gear assembly 208 has a rectangular portion 236 that is positioned within the slot 34 of mounting shaft 16. The rectangular portion 236 engages the sides of slot 34 and thereby constrains the gear assembly 208 and prevents it from rotating relative to the mounting shaft 16. The gear assembly 208 also has an arcuate portion 238 extending above slot 34. The radius of the arcuate portion 238 being substantially the same as the radius of the mounting shaft 16, and the arcuate portion 238 generally extending above slot 34 such that the outer arcuate surface 240 is flush with the outer surface of the mounting shaft 16. By extending the arcuate portion 238 above slot 34, the drive shaft 206 avoids contact with the guiding catheter 5 and pillow block 210.

This embodiment is advantageous in that it allows the user to adjust the rotational facing of the ultrasound element 220 using the second adjusting knob with the same hand used to manipulate the distal end of the guiding catheter with the first adjusting knob. Thus, the need for a separate handle attached to the ultrasound catheter used to rotate the ultrasound catheter relative to the guiding catheter is eliminated.

Figure 41:
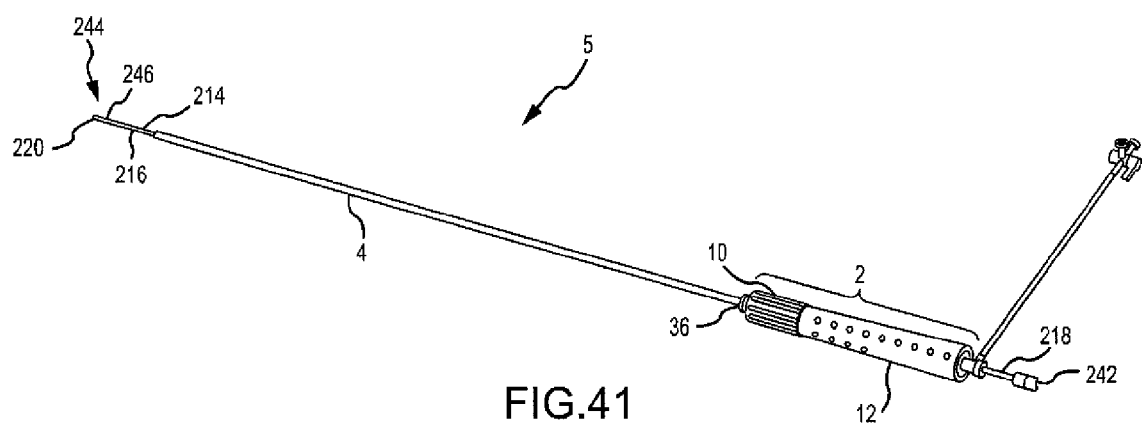
FIG. 41 is an isometric view of one embodiment of the handle of the present invention having an ultrasound catheter disposed therein.
Figure 42:
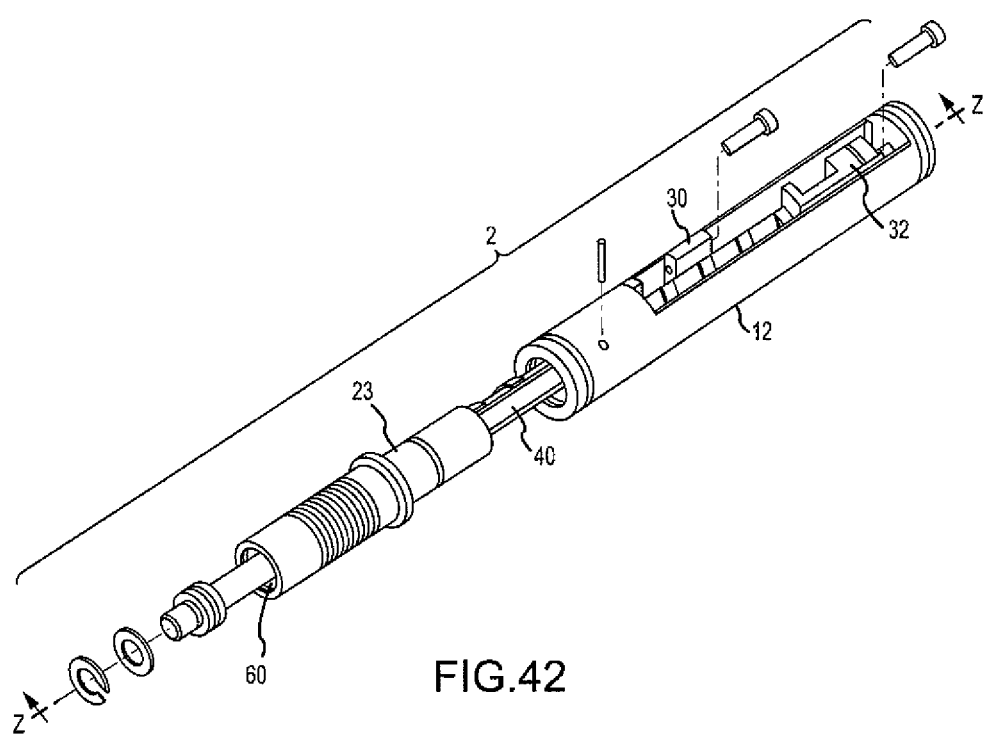
FIG. 42 is an exploded view of one embodiment of the handle of the invention.
Figure 43:
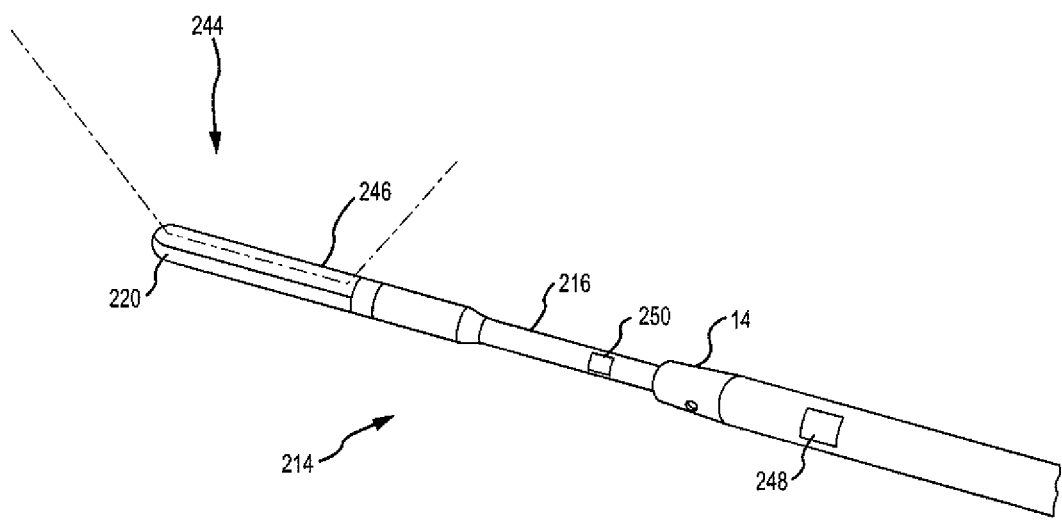
FIG. 43 is an isometric view illustrating the distal end of an embodiment of the invention having an ultrasound catheter disposed within the guiding catheter.

In another embodiment, as depicted in FIGS. 41-43, the handle 2 having a single adjusting knob 10 and a through lumen, as previously discussed, can be used with a diagnostic ultrasound catheter 196. In this embodiment, ultrasound catheter 196 further includes a handle 242 attached to the proximal end 218 of the of the flexible body 216.

The flexible body 216 of the ultrasound catheter 196 is slideably disposed through the lumen of the guiding catheter 5 in a coaxial configuration. In one embodiment, both the ultrasound catheter 196 and the guiding catheter 5 and handle 2 are steerable and/or deflectable. In this embodiment, the ultrasound catheter 196 and the guiding catheter 5 include one or more steering wires or pull wires (not shown) within the flexible bodies 216, 4 of the ultrasound catheter 196 and the guiding catheter 5, respectively. The handle 242 of the ultrasound catheter 196 and the handle 2 of the guiding catheter 5 include actuators for steering and/or deflecting the catheters.

In another embodiment, the handles 2, 242 are different in size and/or shape so that a practitioner can easily distinguish one from the other during a medical procedure. In a further embodiment, the handles 2, 242 are tactilely unique, meaning they each have a different feel or texture relative to the other. For example, one handle may have a soft or spongy surface while the other handle has a hard or stiff surface. Alternatively, one handle may have a smooth surface compared to a rough or textured surface on the other handle. It is advantageous to provide a system in which the handles 242, 2 on the ultrasound catheter 196 and the guiding catheter 5 are different in size, shape and/or tactility to permit a practitioner to easily and quickly identify and distinguish the handle for controlling the ultrasound catheter 196 versus the handle for controlling the guiding catheter 5 during a medical procedure. For example, the handle 2 may be an embodiment of the full sized handles previously discussed, while the handle 242 may simply be a knob that is grasped to rotate the ultrasound catheter inside the guiding catheter 5.

Referring to FIGS. 41-43, the ultrasound catheter 196 is configured in a coaxial relationship with both the handle 2 of the guiding catheter 5 and the lumen of the guiding catheter 5. The handle 2 on the guiding catheter 5 may be manipulated to steer and/or deflect the guiding catheter 5 to direct the distal end 307 of the ultrasound catheter to focus fan 312 on a targeted anatomy. The handle 242 on the ultrasound catheter 196 may also be manipulated to steer and/or deflect the ultrasound catheter 196. The guiding catheter 5 provides a pathway for delivering the distal portion 214 of the ultrasound catheter 196 to the desired anatomical area. The guiding catheter 5 also advantageously constrains the ultrasound catheter 196 within the lumen of the guiding catheter so that the ultrasound element 220 can be properly oriented toward the targeted anatomy. More specifically, the distal portion 214 of the ultrasound catheter 196 is advanced distally until the distal portion 214 extends beyond the distal end 14 of the guiding catheter 5. In one embodiment, the distal portion 214 of the ultrasound catheter 196 is advanced about 5 cm to about 15 cm beyond the distal end 14 of the guiding catheter 5.

Alternatively, the ultrasound catheter 196 may be provided in a "pre-advanced" state, such that the distal portion 214 is provided already advanced outside the distal end 14. This advantageously allows the shaft of the ultrasound catheter 196 to have a smaller outer diameter in its middle portion, than would otherwise be required for the distal portion 214 due to the ultrasound elements 220. This in turn allows the guiding catheter 5 to have a smaller lumen and a smaller outer diameter in turn. An ultrasound catheter 196 in a pre-advanced state can be used with embodiments of handle 2 having a second adjusting knob 10*b*, as described above, because the bond between the ultrasound catheter 196 and the hemostasis tube 222 prevents axial movement of the ultrasound catheter relative to the handle 2.

The handle 242 of the ultrasound catheter 196 can be rotated relative to handle 2 causing the distal portion 214 of the ultrasound catheter 196 to also rotate axially within the lumen of the guiding catheter 5. Thus, the guiding catheter 5 allows the user to steer the ultrasound catheter 196 to the desired site by deflecting the distal end 14 using the adjusting knob 10, and also advantageously assists in properly orienting the ultrasound fan 244 of the ultrasound element 220 in relation to the tissue to be visualized.

The combination of the steering elements above is uniquely advantageous, in particular for orienting the ultrasound fan 244 toward targeted anatomy. In particular, in prior art actuators for ultrasound catheters, the operator may bend the distal end of the catheter in a direction to move the catheter into or close to the relevant anatomy, only to find that while the guiding catheter is in position, the ultrasound fan is not oriented toward the targeted anatomy. The operator must rotate or twist the entire catheter to orient the fan in the proper direction. Naturally, when a bent catheter is rotated, the bend causes it to move out of position entirely, as it is no longer oriented correctly. Due to the narrow nature of 2D ultrasound fans, the operator may find himself repeatedly bending and twisting in succession to find the proper orientation, requiring a great deal of skill and experience to accomplish the task in a reasonable amount of time. In some cases, the catheter simply cannot reach the desired position. In contrast, with the present invention, the guiding catheter 5 is actuated to provide the proper bend. If the fan 244 is not properly oriented, the operator simply grasps handle 242 and twists it, or in other embodiments, pivots the second adjusting knob 10*b*. Because guiding catheter 5 does not rotate with the ultrasound catheter 196, the bend is not moved, only the orientation of the fan is changed. Thus, the fan is quite easily oriented toward the targeted anatomy. The inventors have found that these two handles/actuators combine in a surprising way to allow easy and intuitive manipulation of the ultrasound fan 244.

In an embodiment, the ultrasound element 220 of the ultrasound catheter 196 can include a linear phased array of ultrasound elements, e.g., 64 elements. A lens 246 can cover the ultrasound elements, and may be rounded or flat. The lens 246 may be made of materials that transmit sound at a velocity matching the velocity of sound in blood. The ultrasound elements 220 are operatively coupled to an ultrasound system Referring to FIGS. 41 and 43, the ultrasound element 220 is mounted in a housing that is affixed to the distal end 214 of the ultrasound body 216.

In another embodiment, the ultrasound catheter 169 may include an ultrasound element 220 such as a radiofrequency (RF) ultrasound element or a high intensity focused ultrasound element, also referred to as a HIFU ultrasound element, that, in some cases, may utilize a linear phased array transducer. An RF ultrasound element is a conductive metal having, in one embodiment, a concave surface as described above. The metal may be any conductive metal or a metal alloy consisting of one or more of gold, silver, platinum, iridium, titanium, tantalum, zirconium, vanadium, niobium, hafnium, aluminum, silicone, tin, chromium, molybdenum, tungsten, manganese, beryllium, cobalt, nickel, palladium, osmium, rhenium, technetium, rhodium, ruthenium, cadmium, zinc, germanium, antimony, bismuth, boron, scandium and metals of the lanthanide and actinide series, or any other biocompatible material. In some embodiments, it may be desirable to include a layer of biocompatible materials covering the conductive metal. In another embodiment, the ultrasound catheter 196 may incorporate other types of ultrasound elements suitable for forming ablation lesions such as a microwave transmitter, a cryogenic element, an optical element, or an acoustic transducer, for example a high intensity focused ultrasound transducer.

The ultrasound catheters described and depicted herein are directional. In other words, successful diagnostic imaging depends on proper orientation of the ultrasound element 220 relative to the target tissue.

In one embodiment, the guiding catheter 5, the ultrasound catheter 196, or both may include one or more electrodes 248 coupled to the flexible body 4, 216. Alternatively, the flexible bodies 4, 216 can include a magnetic tracking coil (not shown). The electrode 248 or magnetic tracking coil may be used in conjunction with an electroanatomical mapping system to provide location information for the guiding catheter or ultrasound catheter. Suitable systems include the St Jude Medical Ensite™ Electroanatomical Modeling System, the Biosense Webster Carto™ System, a fluoroscopy system, a magnetic location system such as the gMPS system form Mediguide Ltd. Likewise, the flexible bodies 4, 216 may include one or more radiopaque portions for tracking in a fluoroscopy system. As described above, such systems include the EnSite NavX™ System commercially available from St. Jude Medical, Inc. and as generally shown with reference to commonly assigned U.S. Pat. No. 7,263,397 entitled "Method and Apparatus for Catheter Navigation and location and Mapping in the Heart," the disclosure of which is hereby incorporated by herein by reference in its entirety. Alternative systems include Biosense Webster Carto™ System, commonly available fluoroscopy systems or a magnetic location system such as the gMPS system from Mediguide Ltd., and as generally shown with reference to U.S. Pat. No. 7,386,339, entitled "Medical Imaging and Navigation System," the disclosure of which is incorporated herein by reference in its entirety.

In a further embodiment, to assist in orienting and locating the distal end of the ultrasound catheter 196, the ultrasound catheter 196 can include one or more electrodes 250 disposed on the distal portion 214 of the ultrasound body 216 (see FIG. 39, for example). The electrodes 250 may advantageously be used to orient the ultrasound catheter 196 to ensure that the fan 244 emitted by the ultrasound element 220 is facing or oriented towards the target anatomy. In a particular configuration, the electrodes 250 may be unipolar or bipolar electrogram (EGM) electrodes adapted to measure electrical activity present on a surface of the tissue. For example, in one embodiment, a pair of bipolar electrodes 250 is disposed on an outer surface of the distal end 214, the electrodes in the pair being disposed on opposite sides of the ultrasound element 220. In another embodiment, two pairs of bipolar electrodes 250 are used. The electrodes 250 are disposed on opposite sides of the ultrasound element 220 in a lateral direction generally perpendicular to a central axis of the elongate body of the ultrasound catheter 196. Alternatively, or in addition to the foregoing, a bipolar pair of electrodes 250 may be disposed on opposite sides of the ultrasound element 220 in a lateral direction generally parallel to a central axis of the catheter body. In one embodiment, a side portion of the electrodes 250 is covered in a biocompatible material to prevent pacing and/or sensing of tissue that may contact the side portion of the electrodes 250.

The electrodes 250 can be coupled to an EGM-measurement circuit and a display or user interface for displaying EGM data. The electrodes 250 can be used for diagnostic purposes, for example, to confirm that an effective lesion has been created. In this embodiment, the electrodes 250 are coupled to an impedance-measuring circuit. An ablation lesion is non-conductive scar tissue; thus, the lesion blocks electrical signals. Because impedance measures resistance, the effectiveness of an ablation lesion can be determined based on impedance measurements. Impedance can be measured before, during or after applying ablative energy to the tissue. If an effective lesion has been created, the impedance will be higher after ablation compared to pre-ablation impedance measurements, as generally shown in commonly assigned U.S. patent application Ser. No. 12/622,488, entitled "System and method for assessing lesions in tissue," the disclosure of which is hereby incorporated by reference in its entirety. Likewise, the electrodes 250 can be used to determine the proximity of the catheter to tissue, as generally shown in commonly assigned U.S. patent application Ser. No. 12/650,060, entitled "System and method for assessing coupling between an electrode and tissue," the disclosure of which is hereby incorporated by reference in its entirety.

In another embodiment, the ultrasound catheter 196 includes one or more temperature sensors (not shown), such as thermistors or thermocouples, disposed on the distal portion 307 of the ultrasound body 216. The one or more temperature sensors are positioned to measure the temperature of the ultrasound element 220, and/or the tissue. In one embodiment, temperature sensors are positioned distally and/or proximally of the ultrasound element 220. Temperature readings from the one or more temperature sensors may be output and presented as advisory data to a user (analogous to the above relating to the state of the electrode(s)). For example, temperature readings may be presented via a display (e.g., a color, number, or symbol), a tone (e.g., an audible alarm), and/or haptic or vibratory feedback. In addition, the temperature data may be used to assist in lesion assessment.

Figure 44:
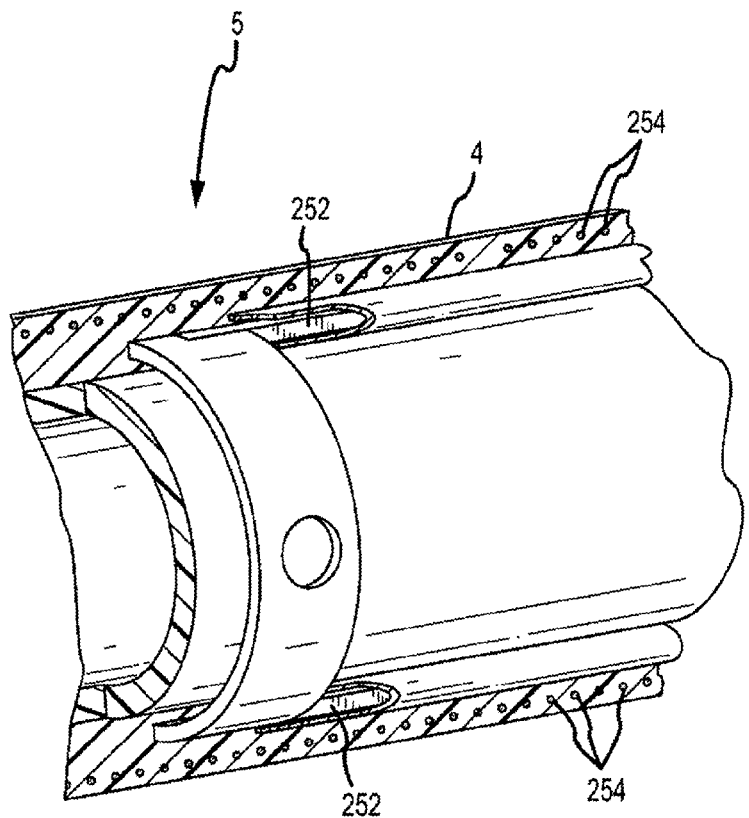
FIG. 44 is a sectional view of a flexible body of an embodiment illustrating flat wires and a braided wire assembly.
Figure 45:
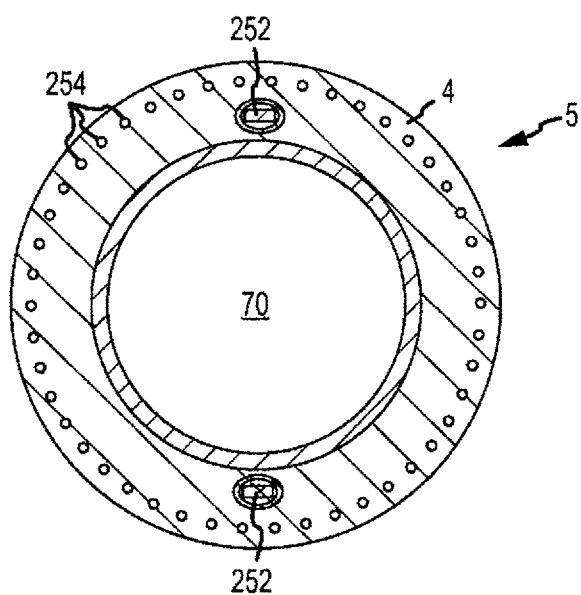
FIG. 45 is a cross-sectional view of a flexible body of an embodiment further illustrating flat wires and a braided wire assembly.

In another embodiment, as depicted in FIGS. 44 and 45, the diameter of the guiding catheter 5 can be reduced when the pull wires 38a, 38b are flat wires 252 having a generally rectangular cross section taken orthogonally to the longitudinal axis of the flat wire 252. The flat wire 252 is preferably composed of stainless steel, although alternative materials used for conventional round pull wires are also suitable. The flat wires 252 preferably has dimensions of about 0.002 inches by about 0.006 inches, and more preferably about 0.004 inches by 0.012 inches. Flat wires 252 allow the outer diameter of guiding catheter 5 to be reduced which is beneficial in that it allows the sheath to be used in smaller body lumens. An exemplary guiding catheter containing flat wires is described in U.S. patent application Ser. No. 11/647,313 entitled "Steerable Catheter Using Flat Pull Wires and Method of Making Same," the disclosure of which is incorporated herein by reference in its entirety.

In yet another embodiment, guiding catheter 5 can include a braided wire assembly 254 to strengthen the guiding catheter 5. The braided wire assembly 254 can be formed of stainless steel wire, including for example 0.003 inch high tensile stainless steel wire. Braided wire assembly 254 can be formed in a standard braid pattern and density, for example, about 16 wires at about 45 to about 60 picks per inch ("PPI") density. Alternatively, a braid may be used that is characterized by a varying braid density. For example, braided wire assembly 254 can be characterized by a first braid density at the proximal end of catheter 5 and then transition to one or more different braid densities as braided wire assembly 254 approaches the distal end 14 of the guiding catheter 5. The braid density of distal end 14 can be greater or less than the braid density at the retaining nut 36. In one example, the braid density at the retaining nut 36 is about 50 PPI and the braid density at the distal end 14 is about 10 PPI. In other embodiments, the braid density at the distal end 14 is about 20% to about 35% of the braid density at the retaining nut 36.

The braided wire assembly 254 can be designed to have transitional braid densities starting at one braid density and transitioning to a lower braid density. In one embodiment, the braid may begin at a braid density of about 50 to 60 PPI, and more preferably between about 50 and about 55 PPI, and then transition to a braid density at the distal end 14 of about 5 to about 15 PPI. The braid density may transition slowly, or it may change using one or more segments. For example, there can be an intermediate zone with a braid density of about 30 to 45 PPI. Variations in the braid density of the braided wire assembly 254 can be used to increase or decrease the flexibility of the guiding catheter 5 and to decrease the overall diameter of the guiding catheter 5 in sections having a decreased braid density. An exemplary guiding catheter containing a braided wire assembly is described in U.S. patent application Ser. No. 11/647,313 entitled "Steerable Catheter Using Flat Pull Wires and Method of Making Same," the disclosure of which is incorporated herein by reference in its entirety.

Figure 46:
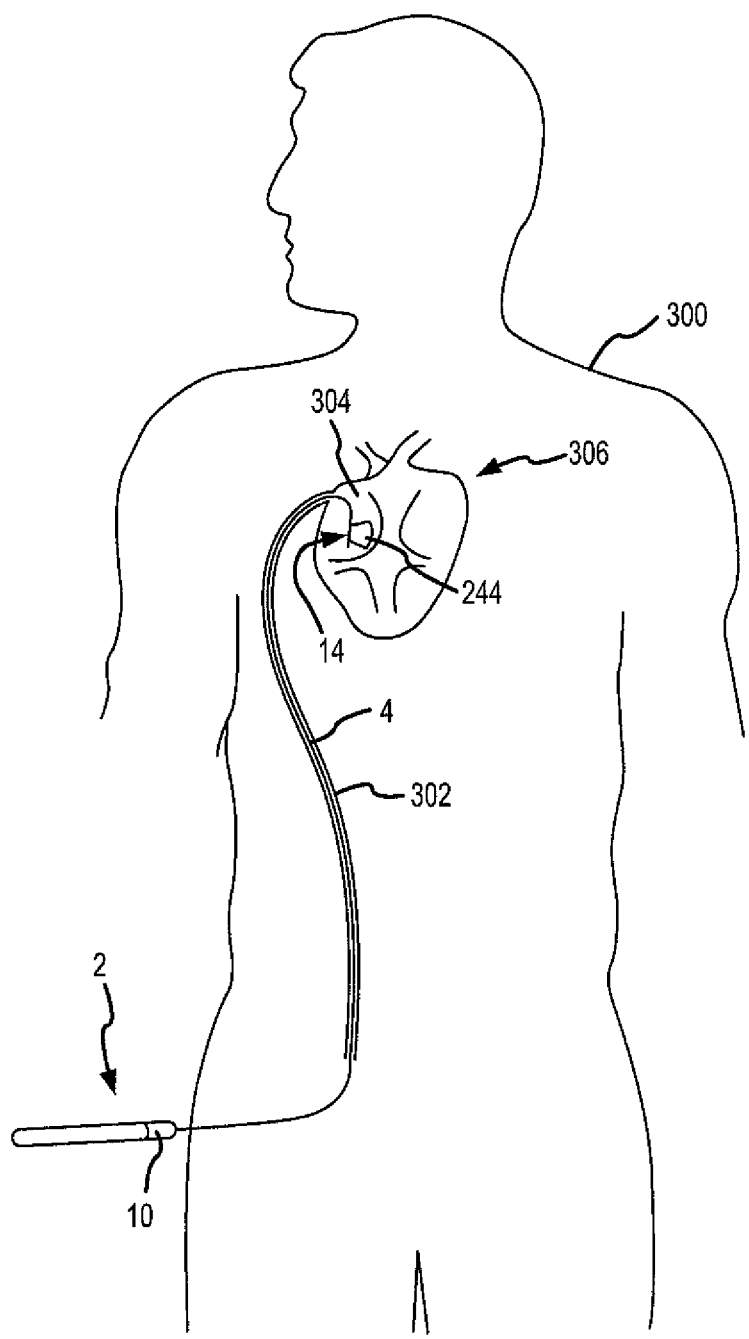
FIG. 46 is a diagrammatic illustration of the control handle of the subject invention being employed in a surgical procedure on a patient.

As can be understood from FIG. 46, which is a diagrammatic illustration of the control handle 2 of the subject invention being employed in a surgical procedure on a patient 300, the distal end 14 of the guiding catheter body 4 is inserted into the patient 300 (e.g., intravenously via a body lumen 302 of the patient 300, percutaneously, or via other avenues for entering the patient's body). The distal end 14 of the catheter body 4 is advanced until positioned in a selected location within the patient 300 (e.g., within a chamber 304 of the patient's heart 306 or other organ, with a body cavity of the patient, etc.). The distal end 14 of the catheter body 4 is then deflected by rotating adjustment knob 10,10*a* about the longitudinal axis of the handle 2. As can be understood from FIGS. 1-44, this causes the slides 30, 32 within the handle 2 to displace along the longitudinal axis in opposite directions. Since each slide 30, 32 is coupled to its respective deflection wire 38 and each deflection wire runs through the guiding catheter body 4 and is coupled to the distal end 14, the distal end 14 of the catheter body 4 is deflected. The orientation of the ultrasound fan 244 can then be adjusted by rotating the ultrasound catheter 196 relative to the guiding catheter 5. The ultrasound adjustment can be accomplished in one embodiment by rotating adjusting knob 10*b* about the longitudinal axis of handle 2 to, in a preferred embodiment, a 1:1 angular rotation of the ultrasound fan about the longitudinal axis of the distal end 14 of the guiding catheter 5. In another embodiment, the ultrasound adjustment can be accomplished by rotating handle 242 relative to handle 2 causing the ultrasound catheter 196 to rotate within the lumen of the guiding catheter 5. In both embodiments, the adjustment of the ultrasound fan 244 orientation can be accomplished without changing the deflection of the distal end 14 of the guiding catheter 5.

Although a number of embodiments of this invention have been described above with a certain degree of particularity, those skilled in the art could make numerous alterations to the disclosed embodiments without departing from the spirit or scope of this invention. For example, all joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A catheter system comprising:
a guiding catheter, the guiding catheter comprising a flexible body having a lumen therethrough and a deflection wire;
the flexible body having a distal end portion and a proximal end portion, with the proximal end portion being coupled to a handle and the distal end being operably connected to the deflection wire;
the handle comprising a first actuator, a second actuator, and a handle grip; the handle having a continuous lumen extending through the first actuator, the second actuator, and the handle grip;
the handle grip including a slide, the slide being operably coupled to the deflection wire; the handle grip further including a rotation assembly being operably connected to the second actuator;
an instrument catheter comprising an instrument element and an elongate body having proximal and distal end portions; the instrument element being attached to the distal end portion;
the instrument catheter being disposed within the lumens of the guiding catheter and handle; the proximal end portion of the instrument catheter extending through the proximal end of the handle;
wherein rotation of the first actuator engages the slide causing the slide to displace axially imparting a tensile force to the deflection wire thereby causing the distal end portion of the guiding catheter and the portion of the instrument catheter contained therein to deflect from a prior configuration, and rotation of the second actuator causes the instrument catheter to rotate within the lumens of the guiding catheter and handle without substantially changing the deflection of the guiding catheter.

2. The system of claim 1 wherein the guiding catheter further comprises a plurality of deflection wires.

3. The system of claim 2 wherein the guiding catheter further comprises a plurality of slides, each slide being operably connected to one of the plurality of deflection wires.

4. The system of claim 1, the proximal portion of the elongate body of the instrument catheter being fixedly attached to the rotation assembly, wherein rotation of the second actuator imparts a torque to the elongate body of the instrument catheter through the rotation assembly thereby causing the rotation of the instrument catheter within the lumens of the guiding catheter and handle.

5. The system of claim 1 wherein the instrument element is an ultrasound element.

6. The system of claim 1, the distal end portion of the instrument catheter further including one of an electrode or a magnetic tracking coil operably connected to an electroanatomical mapping system.

7. The system of claim 1, the distal end portion of the guiding catheter further including one of an electrode or a magnetic tracking coil operably connected to an electroanatomical mapping system.

8. The system of claim 1, wherein the rotation assembly comprises a drive gear, one or more ratio gears, and a positioning gear; the drive gear operably coupled to the second actuator to receive a torque; the one or more ratio gears disposed to engage the drive gear and positioning gear thereby transferring torque from the drive gear to the positioning gear; the positioning gear being coupled to the proximal end portion of the instrument catheter thereby causing the instrument catheter to rotate with the positioning gear.

9. The system of claim 1, wherein the rotation assembly causes a substantially one to one ratio between angular displacement of the second actuator and angular displacement of the instrument catheter.

10. The system of claim 1, wherein the instrument catheter rotates in the same direction as the rotation of the second actuator.

11. The system of claim 1, the handle further comprising an irrigation lumen operably coupled to the proximal end portion of the guiding catheter to maintain a fluid relationship between the irrigation lumen and the lumen of the guiding catheter.

12. The system of claim 1, wherein the deflection wire is a flat wire.

13. The system of claim 1, wherein the guiding catheter includes a braided wire assembly having a variable braid density.

14. The system of claim 13, wherein the braid density of the braided wire assembly at the distal end portion is about 20% to about 35% of the braid density at the proximal end portion.

15. The system of claim 1, wherein the instrument catheter includes a braided wire assembly having a variable braid density.

* * * * *